(12) United States Patent
Dagotturen et al.

(10) Patent No.: US 11,331,360 B2
(45) Date of Patent: May 17, 2022

(54) COMMIPHORA MOLMOL (MYRRH) RESIN EXTRACTS AND USES THEREOF FOR WOUND HEALING AND TREATMENT AND PREVENTION OF MUCOSITIS AND OTHER DISEASES

(71) Applicant: Umayana LLC, Lafayette, CA (US)

(72) Inventors: Hulya Dagotturen, Istanbul (TR); Gulbin Hoeberechts, Lafayette, CA (US)

(73) Assignee: Umayana LLC, Lafayette, CA (US)

( * ) Notice: Subject to any disclaimer, the term of this patent is extended or adjusted under 35 U.S.C. 154(b) by 0 days.

(21) Appl. No.: 17/282,716

(22) PCT Filed: Oct. 4, 2019

(86) PCT No.: PCT/US2019/054839
§ 371 (c)(1),
(2) Date: Apr. 2, 2021

(87) PCT Pub. No.: WO2020/072987
PCT Pub. Date: Apr. 9, 2020

(65) Prior Publication Data
US 2021/0353700 A1    Nov. 18, 2021

Related U.S. Application Data

(60) Provisional application No. 62/742,262, filed on Oct. 5, 2018.

(51) Int. Cl.
| | |
|---|---|
| A61K 36/328 | (2006.01) |
| A61P 29/00 | (2006.01) |
| A61K 9/00 | (2006.01) |
| A61K 9/06 | (2006.01) |
| A61K 31/343 | (2006.01) |
| A61K 47/02 | (2006.01) |
| A61K 47/12 | (2006.01) |
| A61K 47/36 | (2006.01) |

(52) U.S. Cl.
CPC ............ *A61K 36/328* (2013.01); *A61K 9/006* (2013.01); *A61K 9/06* (2013.01); *A61K 31/343* (2013.01); *A61K 47/02* (2013.01); *A61K 47/12* (2013.01); *A61K 47/36* (2013.01); *A61P 29/00* (2018.01); *A61K 2236/17* (2013.01); *A61K 2236/33* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 6,077,513 A | * | 6/2000 | Massoud | A61P 33/10 424/748 |
| 2013/0034529 A1 | | 2/2013 | Alzahrani et al. | |
| 2014/0023721 A1 | | 1/2014 | Amelotti et al. | |
| 2016/0324971 A1 | | 11/2016 | Kilic | |

FOREIGN PATENT DOCUMENTS

| | | |
|---|---|---|
| CN | 104706553 A | 6/2015 |
| WO | 2009/106963 A2 | 9/2009 |

OTHER PUBLICATIONS

International Search Report in International Application No. PCT/US2019/054839, dated Dec. 20, 2019.

\* cited by examiner

*Primary Examiner* — Russell G Fiebig
(74) *Attorney, Agent, or Firm* — Cognition IP, P.C.; Edward Steakley

(57) ABSTRACT

Provided herein are compositions comprising acidic extracts of *Commiphora molmol* (Myrrh) resin for the treatment and prevention of oral mucositis, mucosal infections, topical inflammations, bed sores, decubitis, inflammations of the gastrointestinal tract, canker sores, dental mouth lining ulcers, Behcet disease, and for acute and chronic wound healing. Also provided are methods for producing the disclosed compositions.

55 Claims, 11 Drawing Sheets

COMMIPHORA MOLMOL (MYRRH) RESIN EXTRACTS AND USES THEREOF FOR WOUND HEALING AND TREATMENT AND PREVENTION OF MUCOSITIS AND OTHER DISEASES

CROSS-REFERENCE TO RELATED APPLICATIONS

This application is a 35 U.S.C. § 371 national stage application of PCT International Application No. PCT/US2019/054839, filed on Oct. 4, 2019, which claims the benefit of U.S. Provisional Application No. 62/742,262, filed on Oct. 5, 2018, the contents of which are incorporated herein.

FIELD

Compositions comprising apple cider vinegar extracts of *Commiphora molmol* (myrrh) resin are disclosed. The disclosed compositions are enriched in terpenes and polysaccharides, have increased mucoadhesiveness properties, and may be formulated as solutions, drinks, food products, gels, creams, ointments or toothpastes, for the treatment and prevention of oral mucositis, mucosal inflammations of the gastrointestinal tract, canker sores, dental mouth lining ulcers, Behcet disease, topical inflammations, and for acute or chronic wound healing.

BACKGROUND

Mucositis is the painful inflammation and ulceration of the mucous membranes lining the digestive tract, usually as an adverse effect of chemotherapy and radiotherapy treatment for cancer. Oral and gastrointestinal (GI) mucositis affects almost all patients undergoing high-dose chemotherapy and hematopoietic stem cell transplantation (HSCT), 80% of patients with malignancies of the head and neck receiving radiotherapy, and a wide range of patients receiving chemotherapy, even long after therapy is concluded. Alimentary tract mucositis increases mortality and morbidity and contributes to rising health care costs associated with symptom management, nutritional support, management of secondary infection and hospitalization.

Oral mucositis, the inflammation and ulceration that occurs in the mouth, is a common and often debilitating complication of cancer treatment. Cell death and DNA damage resulting from exposure to radiations and/or chemotherapy causes the release of free radicals, which in turn activate transcription factors and up-regulate pro-inflammatory cytokines, such as TNF-α, ceramide, nitric oxide and matrix metalloproteinases. The inflammatory process leads to the thinning of the mucosal lining of the mouth, with consequent inflammation, ulceration, and release of pro-inflammatory macrophages. Ulcers may range from 0.5 cm to greater than 4 cm in size, and may be covered by a pseudo membrane, a yellowish white fibrin clot. Oral mucositis can be severely painful, and patients may experience trouble speaking, eating, or even opening the mouth. Sores or ulcerations are prone to be infected by virus, bacteria, fungi and oral flora, which in some cases may cause septicemia. Dysgeusia, an alteration in taste perception, is also a common symptom. Thus, oral mucositis can be a dose-limiting condition in chemotherapy and radiation therapy, disrupting a subject's optimal cancer treatment plan and decreasing their chances of survival.

Palifermin, a keratinocyte growth factor, which enhances epithelial cell proliferation, differentiation, and migration, is the only FDA-approved drug for blood cancer subjects undergoing high-dose chemotherapy followed by bone marrow transplant.

Myrrh (*Commiphora molmol*) resin is obtained by incision or produced by spontaneous exudation from the stem and branches of *Commiphora molmol* Engler and/or other species of *Commiphora*. Alcohol myrrh extracts has been traditionally used as tinctures for treatment of infected wounds and skin inflammation. However, alcohol denatures the polysaccharides and other aromatic components found in myrrh. In addition, alcohol causes pain and irritates the skin and the mucosa upon application.

Therefore, a need exists for myrrh formulations with high anti-inflammatory and mucoadhesive properties that are suitable for application to oral and mucosal cavities, the GI tract and wounds, and can consistently heal wounds and ulcerations without exacerbating pain. The present application presents a solution to the aforementioned challenge. In particular, the present inventors have successfully devised acetic acid myrrh resin extract compositions with increased mucoadhesiveness and healing properties. The disclosed myrrh resin extracts provide the polysaccharides and terpenes naturally found in myrrh in amounts sufficient to increase mucoadhesiveness, and their natural low pH enhances acute and chronic wound and ulcer healing.

SUMMARY

It is shown herein that compositions comprising acetic acid myrrh resin extracts are enriched in sesquiterpenes and polysaccharides, heal oral mucositis, and enhance inflammation and wound healing. Based on these findings, acetic acid extracts of myrrh resin comprising polysaccharides and sesquiterpenes are provided.

In some examples, the acetic acid extracts of myrrh resin contain sesquiterpenes in a concentration of about 40% to about 80% (w/w).

In some examples, the sesquiterpenes may comprise 40-50% (w/w) furanoeudesma-1,3-dien, 10-15% (w/w) lindestrene and 5-10% (w/w) curzerene.

In some examples, the acetic acid extracts of myrrh resin contain polysaccharides in a concentration of about 20% to about 40% (w/w).

In some examples, the polysaccharides may comprise one or more of ribofuranose, arabinopyranose, ribopyranose, uronic acid, mannopyranose, allofuronase, galacturonic acid, galactopyranose and allopyranose.

In some examples, the acetic acid is in form of vinegar. In some examples, the vinegar is unpasteurized and unfiltered apple cider vinegar. In some examples, the acetic acid extract of myrrh resin comprises myrrh resin and apple cider vinegar in a ratio of 1:4.

Also provided herein are compositions, which comprise the disclosed acetic acid extracts of myrrh resin, hydrocolloids and pH adjusters.

In some examples, the hydrocolloid is one or more of starch, xanthan gum, guar gum, locust bean gum, gum karaya, gum tragacanth, gum Arabic, cellulose, alginate, pectin, carrageenan, gelatin, gellan and agar.

In some examples, the pH adjuster is one or more of ammonium bicarbonate, ammonium carbonate, ammonium citrate, ammonium hydroxide, ammonium phosphate, calcium carbonate, calcium chloride, calcium citrate, calcium fumarate, calcium hydroxide, calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

In some examples, the hydrocolloid is xanthan gum and the pH adjuster is calcium carbonate.

In some examples, the composition has a pH between about 3.0 and 5.0. In some examples, the composition has a pH between about 3.5 and 4.5. In some examples, the composition comprises about 5 to 50% (w/w) of myrrh resin extract; about 1 to about 5% (w/w) of xanthan gum; and about 0.1 to about 1.0% of calcium carbonate. In some examples, the composition comprises about 30% (w/w) of myrrh resin extract; about 3% (w/w) of xanthan gum; and about 0.5% of calcium carbonate.

In some examples, the composition may further comprise a preservative. The preservative may be one or more of a benzoate, a nitrite, a sulphite and a sorbate. In some examples, the preservative is sodium benzoate.

In some examples, the compositions are Newtonian fluids in form of mouthwashes, creams, gels, food products or wound healing compositions.

In some examples, the mouthwash may further comprise an excipient. In some examples, the excipient is one or more of betaine anhydrous, glycerin, a thymol extract, a clove extract, a mint extract, a fruit flavor, and a *Stevia* powder.

In some examples, the mouthwash comprises betaine anhydrous in a concentration between about 2% and about 6% (w/w); glycerin in a concentration between about 1% and about 10% (w/w); a thymol extract in a concentration between about 0.01% and about 0.1% (w/w); a clove extract in a concentration between about 0.5% and about 1% (w/w); a mint extract in a concentration between about 0.5% and about 1% (w/w); a fruit flavor in a concentration between about 0.5% and about 1% (w/w); and a *Stevia* powder in a concentration between about 0.1% and about 0.5% (w/w).

In some examples, the disclosed creams may further comprise an excipient in a concentration between about 10% and about 18% (w/w). In some examples, the excipient is one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

In some examples, the disclosed creams comprise zinc oxide in a concentration between about 5% and about 10% (w/w); *Hypericum perforatum* oil in a concentration between about 4% and about 8% (w/w); Cera alba in a concentration between about 3% and about 8% (w/w); *Prunus amygdalus sativa* kernel oil in a concentration between about 2% and about 5% (w/w); *Theobroma cacao* seed butter in a concentration between about 2% and about 5% (w/w); and allantoin in a concentration between about 0.5% and about 1.5% (w/w).

In some examples, the disclosed creams have a density between about 1.059 and about 1.015 g/cm$^3$, and a viscosity between about 130,200 and about 166,700 centipoise at room temperature.

In some examples, the disclosed compositions are in form of gels having a density between about 0.9185 and about 1.0521 g/cm$^3$, and a viscosity between about 30,900 and about 33,900 centipoise at room temperature.

In some examples, the disclosed compositions are in form of food products. The food product may be a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

Also provided herein is a process of preparing an acidic myrrh resin extract enriched in sesquiterpenes and polysaccharides. The process comprises: (1) collecting myrrh resin from *Commiphora molmol*; (2) drying the myrrh resin at a temperature between −10° C. to about −4° C. for a period of time between 24 and 72 hours; (3) dissolving the dried myrrh resin in an acidic solvent to obtain a solution; (4) filtering the solution to collect an extract; (5) filtering the extract; (6) cooling the extract at a temperature between about 20° C. and 25° C.; and (7) adjusting the extract's pH between about 3.0 and about 5.0 to obtain an acidic extract of myrrh resin enriched in sesquiterpenes and polysaccharides.

In some embodiments, the dried myrrh resin is dissolved in the acidic solvent by vigorously agitating the myrrh resin with the acidic solvent for a short period of time (5 to 10 minutes) at room temperature and intermittently freezing the myrrh resin with the acidic solvent at a temperature between −10° C. to about −4° C. for a period of time between 48 and 72 hours.

In some embodiments, the extract is filtered to remove polysaccharides and proteins with a molecular weight between about 10,000 Dalton and about 100,000 Dalton.

In some examples, the process may further comprise (8) adding a hydrocolloid to the extract; and (9) adjusting the extract's pH between about 3.0 and about 5.0 with a pH adjuster to obtain a composition comprising an acidic extract of myrrh resin enriched in sesquiterpenes and polysaccharides.

In some examples, the solvent is acetic acid. In some examples, the acetic acid is in form of vinegar. In some examples, the vinegar is unpasteurized and unfiltered apple cider vinegar. In some examples, the myrrh resin and the apple cider vinegar in the acidic extract are in a ratio of 1:4.

In some examples, the hydrocolloid is one or more of starch, xanthan gum, guar gum, locust bean gum, gum karaya, gum tragacanth, gum Arabic, cellulose, alginate, pectin, carrageenan, gelatin, gellan and agar.

In some examples, the pH adjuster is one or more of ammonium bicarbonate, ammonium carbonate, ammonium citrate, ammonium hydroxide, ammonium phosphate, calcium carbonate, calcium chloride, calcium citrate, calcium fumarate, calcium hydroxide, calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

In some examples, the hydrocolloid is xanthan gum and the pH adjuster is calcium carbonate. In some examples, the acidic extract of myrrh resin has a pH between about 3.5 and 4.5.

In some examples, the compositions thus produced comprise about 5 to 50% (w/w) of myrrh resin extract; about 1 to about 5% (w/w) of xanthan gum; and about 0.1 to about 1.0% of calcium carbonate. In some examples, the compositions thus produced comprise about 30% (w/w) of myrrh resin extract; about 3% (w/w) of xanthan gum; and about 0.5% of calcium carbonate.

In some examples, the disclosed process may further comprise adding a preservative. In some examples, the preservative is one or more of a benzoate, a nitrite, a sulphite and a sorbate. In some examples, the preservative is sodium benzoate.

In some examples, the compositions thus produced are Newtonian fluids in form of mouthwashes, creams, gels, food products, or wound healing compositions.

In some examples, the disclosed process may further comprise adding an excipient and distilled water to the composition to produce a mouthwash.

In some examples, the excipient is one or more of betaine anhydrous, glycerin, a thymol extract, a clove extract, a mint extract, a fruit flavor, and a *Stevia* powder.

In some examples, the disclosed process may further comprise adding an excipient to the composition, heating the composition at 70° C., and cooling the composition to produce a cream.

In some examples, the excipient is one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

In some examples, the disclosed process may further comprise adding a gelling agent to the composition to produce a gel. In some examples, the gel has a density between about 0.9185 and about 1.0521 $g/cm^3$, and a viscosity between about 30,900 and about 33,900 centipoise at room temperature.

In some examples, the disclosed process may further comprise formulating the composition as a food product. The food product may be a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

In additional embodiments, provided herein are methods of treating, preventing, controlling or managing a variety of diseases comprising administering the disclosed acidic myrrh resin compositions.

In one embodiment, provided herein is a method for treating, managing or preventing oral mucositis in a subject in need thereof. The method comprises topically administering to the oral mucosa of the subject a composition comprising the disclosed acidic extract of myrrh resin. In some examples, the composition is a Newtonian fluid in form of a mouthwash, a gel or a food product.

In another embodiment, provided herein is a method of treating, managing or preventing an inflammation, an ulcer or a wound in a subject in need thereof. The method comprises administering to the subject a composition comprising the disclosed acidic extract of myrrh resin.

In some examples, the ulcer is a mucosal ulcer, an oral mucosal ulcer, or a gastrointestinal ulcer.

In some examples, the inflammation is gastrointestinal mucositis, a canker sore, or Behcet disease.

In some examples, the wound is a chronic wound, an abrasion, a furuncle or a skin inflammation.

In yet another embodiment, provided herein is a method of treating, managing or preventing a topical inflammation in a subject in need thereof. The method comprises administering to the subject a composition comprising the disclosed acidic extract of myrrh resin.

Exemplary topical inflammations that can be treated, managed or prevented by the disclosed method include, but are not limited to, bedsores, decubitis and acute and chronic wound inflammation.

In some examples, the composition ares administered to the subject once a day, twice a day, three times a day, or four times a day, in an effective amount from about 350 mg to about 600 mg/day. In some examples, the subject is a mammal. In some examples, the subject is a human subject.

In some examples, the composition is administered to the subject prior to, during or after exposure to radiation or chemotherapy.

The acidic extracts of myrrh resins and compositions provided herein present several attractive features and desirable properties that make them suitable for use to treat a variety of conditions in mammal subject subpopulations, such as human subpopulations. For example, unlike any other myrrh resin extracts, the disclosed acidic extracts of myrrh resins and compositions do not contain alcohol and are enriched in sesquiterpenes and polysaccharides, which have natural mucoadhesive and analgesic properties. Therefore, the disclosed acidic extracts of myrrh resins effectively adhere to ulcers, inflammations and wounds, decrease pain and discomfort, and do not cause any damage to mucosal tissue.

Moreover, the disclosed acidic extracts of myrrh resins and compositions have a low pH and thus enhance healing of ulcers, inflammations and wounds. The healing effect is synergistically increased upon combination of the disclosed acidic extracts of myrrh resins with a hydrocolloid.

In addition, because the disclosed acidic extracts of myrrh resins and compositions provide enhanced healing of oral and gastrointestinal mucositis, therapy with the disclosed acidic extracts of myrrh resins and compositions supports a subject's optimal cancer treatment plan and increases their chances of survival.

The foregoing and other features of the disclosure will become more apparent from the following detailed description of several embodiments, which proceeds with reference to the accompanying figure.

DETAILED DESCRIPTION

Figure 1:
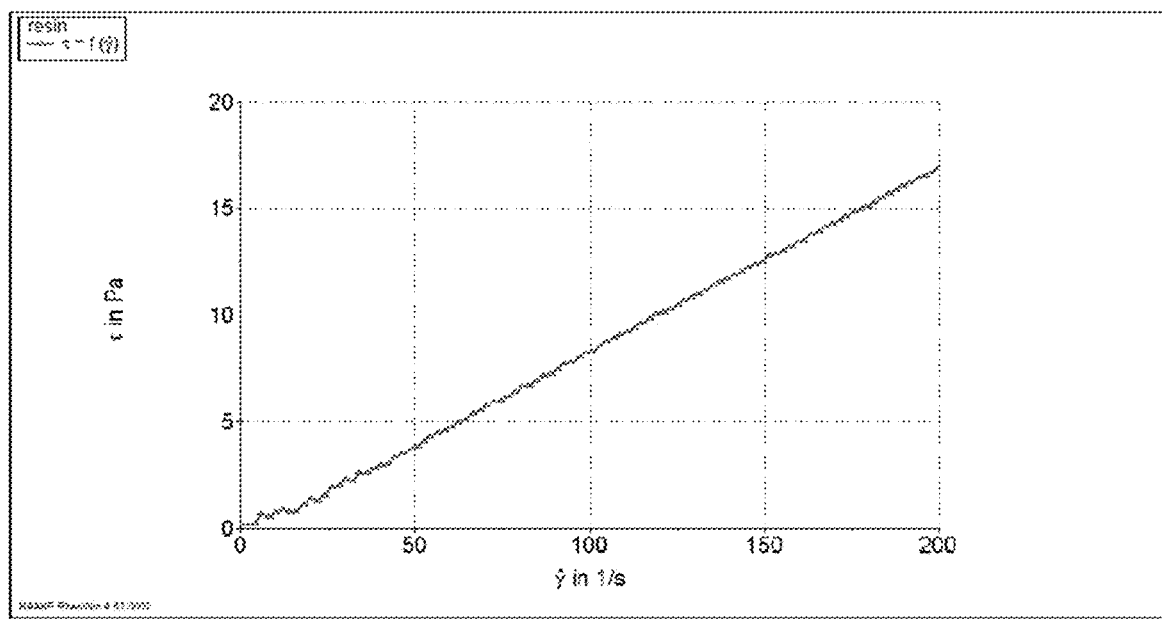
FIG. 1 is a plot showing the flow rate of the acidic myrrh extract. The shear rate of the acidic myrrh extract varies linearly with the flow rate, indicating that the acidic myrrh extract is a Newtonian fluid.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer: To provide or give a subject a composition by an effective route. Application is local. Exemplary routes of application include, but are not limited to, oral and topical routes.

Antibiotic: A chemical substance capable of treating bacterial infections by inhibiting the growth of, or by destroying existing colonies of bacteria and other microorganisms.

Anti-inflammatory agent: An active agent that reduces inflammation and swelling.

Anti-Oxidant: An active agent that inhibits oxidation or reactions promoted by oxygen or peroxides.

Behcet's Disease: A rare disorder that causes blood vessel inflammation throughout the body. Symptoms may include mouth sores, eye inflammation, skin rashes and lesions, and genital sores. Behcet's disease symptoms vary from person to person. Painful mouth sores that look similar to canker sores are the most common sign of Behcet's disease. They begin as raised, round lesions in the mouth that quickly turn into painful ulcers. The sores usually heal in one to three weeks, though they do recur. Some people may develop acne-like sores on their bodies. Others may develop red, raised and tender nodules on their skin, especially on the lower legs. In the genitals, red, open sores commonly occur on the scrotum or the vulva. The sores are usually painful and may leave scars. Behcet's disease may cause inflammation in the eye, with redness, pain and blurred vision in one or both eyes. Joint swelling and pain in the knees, ankles, elbows or wrists also may be involved. The disease may also cause inflammation in blood vessels, with redness, pain, and swelling in the arms or legs when a blood clot results, as well as inflammation in the brain and nervous system that leads to headache, fever, disorientation, poor balance or stroke.

Cancer: A condition characterized by unregulated cell growth. Examples of cancer include, but are not limited to, squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, and various types of head and neck cancer.

Canker Sore or Recurrent Aphthous Stomatitis (RAS): Small, round or oval, painful yellowish sores that usually affect the softer parts of the mouth, such as the tongue, soft palate, cheeks, and lips. Sores usually heal, but then reappear in the same or new locations after a period of time. There are three main forms: (1) Minor Aphthous Stomatitis is the form that affects more than 80% of canker sore sufferers. The sores are usually small (less than 1 centimeter in diameter), heal in about a week, and do not cause scarring; (2) Major Aphthous Stomatitis is a more severe form, with sores that last two weeks or more and are typically over 1 centimeter in diameter. They can be extremely painful and often heal with scarring; (3) Herpetiform Aphthous Stomatitis is characterized by the presence of sores that occur as clusters of very small ulcers (less than a millimeter in some cases) that sometimes merge together to form larger ulcers. The cause of canker sores is not known.

Chemotherapeutic agent or Chemotherapy: A chemical agent with therapeutic usefulness in the treatment of diseases characterized by abnormal cell growth. Such diseases include tumors, neoplasms, and cancer. In one example, a chemotherapeutic agent is a radioactive compound. In one example, a chemotherapeutic agent is a biologic, such as a monoclonal antibody. In some examples, a subject treated with an active agent using the disclosed methods, is, will be, or was previously treated with chemotherapy.

Contacting: Placement in direct physical association; includes both in solid and liquid form.

Control: A reference standard. In some examples, a control is a known value or range of values, such as one indicative of the presence or the absence of a disease. In some examples, a control is a value or range of values, indicating a response in the absence of a therapeutic agent.

Effective amount: The amount of an active agent (alone or with one or more other active agents) sufficient to induce a desired response, such as to prevent, treat, reduce and/or ameliorate a condition. Effective amounts of an active agent, alone or with one or more other active agents, can be determined in many different ways, such as assaying for a reduction in of one or more signs or symptoms associated with the condition in the subject or measuring the level of one or more molecules associated with the condition to be treated.

Hydrocolloid: A substance that produces a gel when dispersed in water.

Inhibiting a condition: Reducing, slowing, or even stopping the development of a condition, for example, in a subject who is at risk of developing or has a particular condition.

Localized application: The application of an active agent in a particular location in the body.

Mouth Ulcer: An ulcer on the mucous membrane of the oral cavity. The most common causes of oral ulceration are local trauma, such as trauma caused by poorly fitted dental prosthesis, traumatizing orthodontic devices or hard toothbrushing, canker sores, radiation therapy, chemotherapy, oral cancer and Behcet's disease.

Mucoadhesive: A substance that strongly attaches to mucosal tissue upon hydration without any additional adhesive material, and remains adhered to the tissue in moist or wet in vivo environments.

Mucosa: A membrane that lines various cavities in the body and covers the surface of internal organs. It consists of one or more layers of epithelial cells overlying a layer of loose connective tissue. The mucosa is mostly of endodermal origin and is continuous with the skin at various body openings such as the eyes, ears, inside the nose, inside the mouth, lip, vagina, the urethral opening and the anus. Some mucous membranes secrete mucus, a thick protective fluid. The function of the membrane is to stop pathogens and dirt from entering the body and to prevent bodily tissues from becoming dehydrated.

Mucosal Administration: Administration through the mouth, nose, vagina, eyes and ears of a subject.

Newtonian Fluid: A fluid that behaves according to Newton's law, with a viscosity μ that is independent of stress, and with a linear relationship between stress and strain rate. Although viscosity changes with temperature, it does not change with the strain rate.

Oral administration: Delivery of an active agent through the mouth.

Organoleptic: A property of an edible substance or liquid that an individual experiences via the senses, including taste, sight, smell, and touch.

pH Adjuster or Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Pharmaceutically acceptable carriers: The pharmaceutically acceptable carriers useful in this disclosure are conventional. The nature of the carrier can depend on the particular mode of administration being employed. For instance, oral applications usually include pharmaceutically and physiologically acceptable fluids such as water, physiological saline, balanced salt solutions, aqueous dextrose, glycerol or the like as a vehicle. In addition to biologically-neutral carriers, oral compositions may also contain minor amounts of non-toxic auxiliary substances, such as wetting or emulsifying agents, preservatives, and pH buffering agents and the like.

Radiation therapy: A use of directed gamma rays or beta rays to induce sufficient damage to a cell so as to limit its ability to function normally or to destroy the cell altogether.

Rheology: The study of flow and deformation of materials under applied forces. The measurement of rheological properties, routinely made by a rheometer, is applicable to fluids, such as dilute solutions of polymers and surfactants, concentrated protein formulations, and semisolids, such as pastes and creams.

Subject: A living multi-cellular vertebrate organism, a category that includes human and non-human mammals, as well as birds (such as chickens and turkeys), fish, and reptiles. Exemplary subjects include mammals, such as human and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Topical administration: Delivery of an active agent to a body surface, such as, the skin or mucosa, as in, for example, topical drug administration in the prevention or treatment of various skin disorders.

Ulcer: A break in the skin or mucous membrane with loss of surface tissue and the disintegration and necrosis of epithelial tissue. A mucosal ulcer specifically occurs on a mucous membrane.

Under conditions sufficient to: A phrase that is used to describe any environment that permits the desired activity.

Viscosity: The measure of a fluid's resistance to gradual deformation by shear stress or tensile stress.

Acidic Extracts of Myrrh Resin and Compositions Thereof

Acidic extracts of myrrh resin are disclosed. Myrrh resin is an exudate obtained from the tree *Commiphora myrrha*, also known as *Commiphora molmol*, which belongs to the family Burseraceae. The genus *Commiphora* includes over 150 species, and it is naturally enriched in sesquiterpenes, such as limonene, curzerene, germacrene B, isocericenine, myrcenol, beta selinene, and spathulenol, and polysaccharides.

To ensure that the extracts maintain its natural sesquiterpene and polysaccharide content, the disclosed extracts are obtained by dissolving myrrh resin in acetic acid. The acetic acid may be in form of unpasteurized and unfiltered apple cider vinegar. Preferably, the apple cider vinegar is made from organic apples, such that it is pesticide-free and contains natural sugars. The acetic acid extract of myrrh resin may comprise myrrh resin and apple cider vinegar in a ratio of 1:4.

Unlike any other myrrh extract known in the art, the disclosed acidic extracts of myrrh resins do not contain alcohol and are enriched in natural sesquiterpenes and polysaccharides, which have mucoadhesive and analgesic properties. In some examples, the disclosed acetic acid extract of myrrh resin contains sesquiterpenes in a concentration of about 40% to about 80% (w/w). The sesquiterpenes may comprise 40-50% (w/w) furanoeudesma-1,3-dien, 10-15% (w/w) lindestrene and 5-10% (w/w) curzerene. In some examples, the disclosed acetic acid extract of myrrh resin contains polysaccharides in a concentration of about 20% to about 40% (w/w). Exemplary polysaccharides include, but are not limited to, one or more of ribofuranose, arabinopyranose, ribopyranose, uronic acid, mannopyranose, allofuronase, galacturonic acid, galactopyranose and allopyranose.

Because of their high sesquiterpene and polysaccharide content, the disclosed acidic extracts of myrrh resins effectively adhere to ulcers, inflammations and wounds, decrease pain and discomfort, and do not cause any damage to mucosal tissue. Moreover, because of the presence of an acidic solvent, the disclosed acidic extracts of myrrh resins have a low pH and thus enhance healing of ulcers, inflammations and wounds.

The disclosed acidic extracts of myrrh resins may be combined with a hydrocolloid and a pH adjuster to synergistically increase their healing properties. Exemplary hydrocolloids include, but are not limited to, one or more of starch, xanthan gum, guar gum, locust bean gum, gum karaya, gum tragacanth, gum Arabic, cellulose, alginate, pectin, carrageenan, gelatin, gellan and agar.

pH adjusters include, but are not limited to, one or more of ammonium bicarbonate, ammonium carbonate, ammonium citrate, ammonium hydroxide, ammonium phosphate, calcium carbonate, calcium chloride, calcium citrate, calcium fumarate, calcium hydroxide, calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

In some examples, acidic myrrh resin extract compositions are provided, wherein the hydrocolloid is xanthan gum and the pH adjuster is calcium carbonate.

The disclosed compositions have a pH between about 3.0 and 5.0. Preferably, the composition has a pH between about 3.5 and 4.5.

In some examples, the disclosed compositions comprise about 5 to 50% (w/w) of myrrh resin extract; about 1 to about 5% (w/w) of xanthan gum; and about 0.1 to about 1.0% of calcium carbonate. In some examples, the disclosed compositions comprise about 30% (w/w) of myrrh resin extract; about 3% (w/w) of xanthan gum; and about 0.5% of calcium carbonate.

The disclosed compositions may further comprise a preservative. Exemplary preservatives include, but are not limited to, one or more of a benzoate, a nitrite, a sulphite and a sorbate. In some examples, the preservative is sodium benzoate.

The disclosed compositions may be formulated as Newtonian fluids in form of mouthwashes, creams, gels, wound healing compositions, drinks or food products.

Mouthwash compositions may further comprise distilled water and an excipient. Exemplary excipients include, but are not limited to, one or more of betaine anhydrous, glycerin, a thymol extract, a clove extract, a mint extract, a fruit flavor, and a *Stevia* powder. In some examples, the mouthwash may comprise betaine anhydrous in a concentration between about 2% and about 6% (w/w); glycerin in a concentration between about 1% and about 10% (w/w); a thymol extract in a concentration between about 0.01% and about 0.1% (w/w); a clove extract in a concentration between about 0.5% and about 1% (w/w); a mint extract in a concentration between about 0.5% and about 1% (w/w); a fruit flavor in a concentration between about 0.5% and about 1% (w/w); and a *Stevia* powder in a concentration between about 0.1% and about 0.5% (w/w).

Cream compositions may comprise an excipient in a concentration between about 10% and about 18% (w/w). Exemplary excipients include, but are not limited to, one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, cococaprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

In some examples, the creams may comprise zinc oxide in a concentration between about 5% and about 10% (w/w); *Hypericum perforatum* oil in a concentration between about 4% and about 8% (w/w); Cera alba in a concentration between about 3% and about 8% (w/w); *Prunus amygdalus sativa* kernel oil in a concentration between about 2% and about 5% (w/w); *Theobroma cacao* seed butter in a concentration between about 2% and about 5% (w/w); and allantoin in a concentration between about 0.5% and about 1.5% (w/w). The creams may have a density between about 1.059 and about 1.015 g/cm$^3$, and a viscosity between about 130,200 and about 166,700 centipoise at room temperature.

Gel compositions may have a density between about 0.9185 and about 1.0521 g/cm$^3$, and a viscosity between about 30,900 and about 33,900 centipoise at room temperature.

Food products may include, but are not limited to, a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

Methods of Producing the Disclosed Acidic Extract of Myrrh Resin and Compositions Thereof Also provided herein is a process for preparing an acidic myrrh resin extract enriched in sesquiterpenes and polysaccharides, and compositions comprising the disclosed acidic myrrh resin extract. The disclosed process comprises: (1) collecting myrrh resin from *Commiphora molmol*; (2) drying the myrrh resin at a temperature between −10° C. to about −4° C. for a period of time between 24 and 72 hours; (3) dissolving the dried myrrh resin in an acidic solvent to obtain a solution; (4) filtering the solution to collect an extract; (5) filtering the extract; (6) cooling the extract at a temperature between about 20° C. and 25° C.; and (7) adjusting the extract's pH between about 3.0 and about 5.0 to obtain an acidic extract of myrrh resin enriched in sesquiterpenes and polysaccharides.

In some embodiments, the dried myrrh resin is dissolved in the acidic solvent by vigorously agitating the myrrh resin with the acidic solvent for a short period of time (5 to 10 minutes) at room temperature and intermittently freezing the myrrh resin with the acidic solvent at a temperature between −10° C. to about −4° C. for a period of time between 48 and 72 hours.

In some embodiments, the extract is filtered to remove polysaccharides and proteins with a molecular weight between about 10,000 Dalton and about 100,000 Dalton.

The acetic acid may be in form of unpasteurized and unfiltered apple cider vinegar. Preferably, the apple cider vinegar is made from organic apples, such that it is pesticide-free and contains natural sugars. The acetic acid extract of myrrh resin may comprise myrrh resin and apple cider vinegar in a ratio of 1:4.

To obtain the disclosed compositions, the process further comprises (8) adding a hydrocolloid to the extract; and (9) adjusting the extract's pH between about 3.0 and about 5.0 with a pH adjuster to obtain compositions comprising acidic extracts of myrrh resin enriched in sesquiterpenes and polysaccharides.

Exemplary hydrocolloids include, but are not limited to, one or more of starch, xanthan gum, guar gum, locust bean gum, gum karaya, gum tragacanth, gum Arabic, cellulose, alginate, pectin, carrageenan, gelatin, gellan and agar.

Exemplary pH adjusters include, but are not limited to, one or more of ammonium bicarbonate, ammonium carbonate, ammonium citrate, ammonium hydroxide, ammonium phosphate, calcium carbonate, calcium chloride, calcium citrate, calcium fumarate, calcium hydroxide, calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

In some examples, the hydrocolloid is xanthan gum and the pH adjuster is calcium carbonate.

The compositions thus produced have a pH between about 3.0 and 5.0, and preferably, a pH between about 3.5 and 4.5. In some examples, the compositions thus produced comprise about 5 to 50% (w/w) of myrrh resin extract; about 1 to about 5% (w/w) of xanthan gum; and about 0.1 to about 1.0% of calcium carbonate. In some examples, the disclosed compositions comprise about 30% (w/w) of myrrh resin extract; about 3% (w/w) of xanthan gum; and about 0.5% of calcium carbonate.

Compositions produced by the disclosed process may further comprise a preservative. Exemplary preservatives include, but are not limited to, one or more of a benzoate, a nitrite, a sulphite and a sorbate. In some examples, the preservative is sodium benzoate.

The compositions thus produced may be formulated as a Newtonian fluid in form of a mouthwash, a cream, a gel, a wound healing composition, a drink or a food product.

Mouthwash compositions may further comprise distilled water and an excipient. Exemplary excipients include, but are not limited to, one or more of betaine anhydrous, glycerin, a thymol extract, a clove extract, a mint extract, a fruit flavor, and a *Stevia* powder. In some examples, the mouthwash may comprise betaine anhydrous in a concentration between about 2% and about 6% (w/w); glycerin in a concentration between about 1% and about 10% (w/w); a thymol extract in a concentration between about 0.01% and about 0.1% (w/w); a clove extract in a concentration between about 0.5% and about 1% (w/w); a mint extract in a concentration between about 0.5% and about 1% (w/w); a fruit flavor in a concentration between about 0.5% and about 1% (w/w); and a *Stevia* powder in a concentration between about 0.1% and about 0.5% (w/w).

In some embodiments, the disclosed process may further comprise adding an excipient to the composition, heating the composition at 70° C., and cooling the composition to produce a cream. Cream compositions may comprise an excipient in a concentration between about 10% and about 18% (w/w). Exemplary excipients include, but are not limited to, one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

In some examples, the disclosed creams may comprise zinc oxide in a concentration between about 5% and about 10% (w/w); *Hypericum perforatum* oil in a concentration between about 4% and about 8% (w/w); Cera alba in a concentration between about 3% and about 8% (w/w); *Prunus amygdalus sativa* kernel oil in a concentration between about 2% and about 5% (w/w); *Theobroma cacao* seed butter in a concentration between about 2% and about 5% (w/w); and allantoin in a concentration between about 0.5% and about 1.5% (w/w). The disclosed creams may have a density between about 1.059 and about 1.015 g/cm$^3$, and a viscosity between about 130,200 and about 166,700 centipoise at room temperature.

In some embodiments, the disclosed process may further comprise adding a gelling agent to the composition to produce a gel. Gel compositions may have a density between about 0.9185 and about 1.0521 g/cm$^3$, and a viscosity between about 30,900 and about 33,900 centipoise at room temperature.

In some embodiments, the disclosed process may further comprise adding various ingredients to the composition to produce a food product. Food products may include, but are not limited to, a dairy product, a yoghurt, an ice cream, a milk-based drink, a milk-based garnish, a pudding, a milk-shake, an ice tea, a fruit juice, a diet drink, a soda, a sports drink, a powdered drink mixture for dietary supplementation, an infant and baby food, a calcium-supplemented orange juice, a sauce or a soup.

Methods of Use of Compositions Comprising the Disclosed Acidic Extract of Myrrh Resin Also provided herein are methods for treating, controlling, managing or preventing a variety of diseases. The disclosed methods comprising locally applying compositions comprising the acidic extracts of myrrh resin once to four times a day in therapeutically effective amounts. The disclosed compositions are Newtonian fluids and may be administered orally or topically in form of a mouthwash, a gel or a food product.

In some embodiments, provided herein is a method for treating, managing or preventing oral mucositis in a subject in need thereof. The method comprises topically administering to the oral mucosa of the subject a composition comprising the disclosed acidic extract of myrrh resin. In some examples, the composition is a Newtonian fluid in form of a mouthwash, a gel or a food product.

In some embodiments, provided herein is a method of treating, managing or preventing an inflammation, an ulcer or a wound in a subject in need thereof. The method comprises administering to the subject a composition comprising the disclosed acidic extract of myrrh resin.

Exemplary ulcers that can be treated, managed or prevented by the disclosed method include, but are not limited to, mucosal ulcers, oral mucosal ulcers, mouth ulcers, and gastrointestinal ulcers.

Mouth ulcers include, but are not limited to, those brought about by local trauma, such as trauma caused by poorly fitted dental prosthesis, traumatizing orthodontic devices or hard toothbrushing, canker sores, radiation therapy, chemotherapy, oral cancer and Behcet's disease.

Exemplary inflammations include, but are not limited to, gastrointestinal mucositis, a canker sore, or Behcet disease.

Exemplary wounds include, but are not limited to, a chronic wound, an abrasion, a furuncle or a skin inflammation.

In yet another embodiment, provided herein is a method of treating, managing or preventing a topical inflammation in a subject in need thereof. The method comprises administering to the subject a composition comprising the disclosed acidic extract of myrrh resin.

Exemplary topical inflammations that can be treated, managed or prevented by the disclosed method include, but are not limited to, bed sores, decubitis and acute and chronic wound inflammation.

The disclosed compositions may be administered to the subject once a day, twice a day, three times a day, or four times a day, in a therapeutically effective amount.

In some embodiments, the subject is a mammal. In some embodiments, the subject is a human subject.

The disclosed compositions may be administered to the subject prior to, during or after exposure to radiation or chemotherapy.

In some embodiments, the disclosed compositions are in form of a mouthwash. Mouthwash compositions may further comprise distilled water and an excipient.

Exemplary excipients include, but are not limited to, one or more of betaine anhydrous, glycerin, a thymol extract, a clove extract, a mint extract, a fruit flavor, and a *Stevia* powder.

In some examples, the mouthwash may comprise betaine anhydrous in a concentration between about 2% and about 6% (w/w); glycerin in a concentration between about 1% and about 10% (w/w); a thymol extract in a concentration between about 0.01% and about 0.1% (w/w); a clove extract in a concentration between about 0.5% and about 1% (w/w); a mint extract in a concentration between about 0.5% and about 1% (w/w); a fruit flavor in a concentration between about 0.5% and about 1% (w/w); and a *Stevia* powder in a concentration between about 0.1% and about 0.5% (w/w).

In some embodiments, the disclosed compositions are in form of creams. Cream compositions may comprise an excipient in a concentration between about 10% and about 18% (w/w).

Exemplary excipients include, but are not limited to, one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, cocoprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

In some examples, the creams may comprise zinc oxide in a concentration between about 5% and about 10% (w/w); *Hypericum perforatum* oil in a concentration between about 4% and about 8% (w/w); Cera alba in a concentration between about 3% and about 8% (w/w); *Prunus amygdalus sativa* kernel oil in a concentration between about 2% and about 5% (w/w); *Theobroma cacao* seed butter in a concentration between about 2% and about 5% (w/w); and allantoin in a concentration between about 0.5% and about 1.5% (w/w).

The disclosed creams may have a density between about 1.059 and about 1.015 g/cm$^3$, and a viscosity between about 130,200 and about 166,700 centipoise at room temperature.

In some embodiments, the disclosed compositions may be in form of gel. Gel compositions may have a density between about 0.9185 and about 1.0521 g/cm$^3$, and a viscosity between about 30,900 and about 33,900 centipoise at room temperature.

In some embodiments, the disclosed compositions may be in form of food products. Food products may include, but are not limited to, a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

The methods provided herein present many advantages that make them suitable for treating, managing or preventing a variety of conditions in mammal subject, such as humans. The disclosed methods make use of acidic extracts of myrrh resins and compositions that do not contain alcohol and are enriched in sesquiterpenes and polysaccharides. Because sesquiterpenes and polysaccharides have natural mucoadhesive and analgesic properties, the compositions administered by the disclosed methods rapidly and effectively adhere to ulcers, inflammations and wounds, decrease pain and discomfort, and do not cause any damage to mucosal tissue.

The disclosed acidic extracts of myrrh resins and compositions have a low pH and thus enhance healing of ulcers, inflammations and wounds. The healing effect is synergistically increased by the combination of the disclosed acidic extracts of myrrh resins with a hydrocolloid.

The enhanced healing effect of the disclosed acidic extracts of myrrh resin compositions supports a subject's optimal cancer treatment plan and increases their chances of survival.

EXAMPLES

Example 1: Preparation and Analysis of Compositions Comprising the Disclosed Acidic Extract of Myrrh Resin Myrrh resin was collected from *Commiphora molmol*, dried and dissolved in unpasteurized and unfiltered apple cider vinegar by vigorously agitating the myrrh resin with the apple cider vinegar for 5 to 10 minutes at room temperature and intermittently freezing the myrrh resin with the apple cider vinegar at a temperature between −10° C. to about −4° C. for a period of time between 48 and 72 hours to obtain a solution. The solution was filtered, cooled, and the pH was adjusted to 3.5 with a pH adjuster before and after adding a hydrocolloid to the solution to form a composition.

Rheological Properties

Samples of the composition thus obtained were tested at 25° C. using a HAAKE™ Viscotester™ iQ Rheometer. For CC25 DIN cylindrical geometry, the A factor was set to 22620 Pa/Nm and the M Factor was set to 12.33 sec-1. For the flow rate of the myrrh solution, the shear rate was subtracted from 0 sn$^-$to 200 sn$^{-1}$ in 120 s and 100 data were taken. FIG. 1 shows the flow curve of the composition. The data show that the shear rate of the composition comprising the disclosed acidic extract of myrrh resin varies linearly with the flow rate, and thus demonstrate that the composition is a Newtonian fluid.

Antimicrobial Properties

The antimicrobial properties of the composition comprising the disclosed acidic extract of myrrh resin were analyzed by minimum inhibitory concentrations. The antibacterial effects of the composition were tested against *Pseudomonas aeruginosa*, *Staphylococcus aureus*, *Enterococcus hirae*, *Aspergillus niger* and *Escherichia coli*. The antifungal effects of the composition were tested against *Candida albicans*. The results, shown in Table 1 below, demonstrate that the composition comprising the disclosed acidic extract of myrrh resin inhibits microbial growth.

TABLE 1

| ANTIMICROBIOLOGIC TEST RESULTS | | | | |
|---|---|---|---|---|
| MICROORGANISMS | BIOLOGIC ACTIVITY | DOSAGE | DURATION | ANTIMICROBIOLOGIC EFFECTIVENESS (%) REDUCTION |
| *Escherichia coli* ATCC 10536 | + | %100 | 5 mins | %99.999 |
| *Staphylococcus* | + | %100 | 5 mins | %99.999 |

TABLE 1-continued

ANTIMICROBIOLOGIC TEST RESULTS

| MICROOGANISMS | BIOLOGIC ACTIVITY | DOSAGE | DURATION | ANTIMICROBIOLOGIC EFFECTIVENESS (%) REDUCTION |
|---|---|---|---|---|
| aureus ATCC 6538 | | | | |
| Pseudomonas aeruginosa ATCC 15442 | + | %100 | 5 mins | %99.999 |
| Enterococcus hirae ATCC 10541 | + | %100 | 5 mins | %99.999 |
| Candida albicans ATCC 10231 | + | %100 | 15 mins | %99.99 |
| Aspergillus niger ATCC 16404 | + | %100 | 15 mins | %99.99 |

Cytotoxicity Analysis

Figure 2:
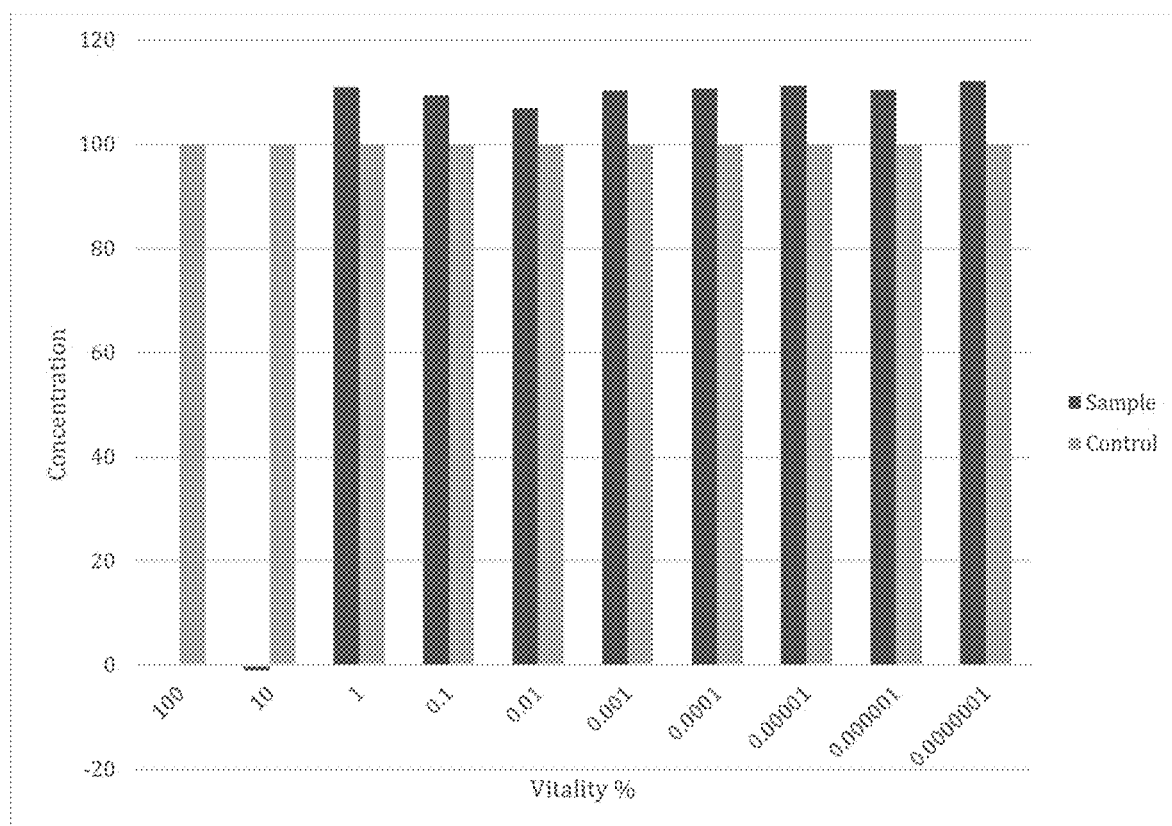
FIG. 2 is a plot showing cytotoxicity indexes of the disclosed acidic myrrh extract gels in 10-fold serial dilutions on the vitality of kidney VERO, CCL-81 cell cultures from *Cercopithecus aethiops*. Left column: sample; right column: control.

Cytotoxicity analysis was performed using the kidney VERO, CCL-81 cell line from *Cercopithecus aethiops*. The cells were grown in Minimum Essential Medium 1× supplemented with 10% Fetal Bovine Serum and Gibco Antibiotic-Antimycotic 100×, plated in 96-well cell culture plates at a density of $1 \times 10^4$ cells/well, and incubated for 24 hours at 37° C. in 5% CO2. At the end of incubation, the composition comprising the disclosed acidic extract of myrrh resin in the form of gel was added to the cell culture in 10-fold serial dilutions, and incubated for 24 hours at 37° C. in 5% CO2. Cytotoxicity was measured by Non-Radioactive Cell Proliferation Assay using MTS (3-(4,5-dimethylthiazol-2-yl)-5-(3-carboxymethoxyphenyl)-2-(4-sulfophenyl)-2H-tetrazolium) and PMS (phenazine methosulfate), and measuring crystal formation by spectrophotometry (490 nm-630 nm wavelength) at the end of incubation with MTS/PMS. The results are shown in FIG. 2. No cytotoxicity was observed at concentrations of 50% or lower of the acidic myrrh resin extract in the composition. At concentrations of 30% and lower, cell proliferation increased by 10%.

Example 2: Treatment of Oral Mucositis in a Subject with Hodgkin's Lymphoma Undergoing High Dose Chemotherapy The efficacy and safety of the compositions comprising the disclosed acidic extract of myrrh resin were clinically assessed for prevention, treatment and/or improvement of oral and gastrointestinal mucositis.

Oral examination of a subject diagnosed with Hodgkin's Lymphoma and undergoing high dose chemotherapy revealed multiple bleeding, ulcerated lesions in the upper and lower lip and in palate. The subject was diagnosed with grade IV mucositis and required parenteral or enteral nutritional support. Treatment of the oral lesions with cryotherapy, sodium bicarbonate, Ad-muc, saline solution and chlorhexidine gluconate was not effective, and the subject was recommended for prophylactic intubation. In place of prophylactic incubation, the subject began using the composition comprising the disclosed acidic extract of myrrh resin in the form of gel four times a day. After a week of applications, the subject showed a strong decrease in mucositis from grade IV to grade II. Mucositis was fully treated after six weeks of use.

Figure 3:
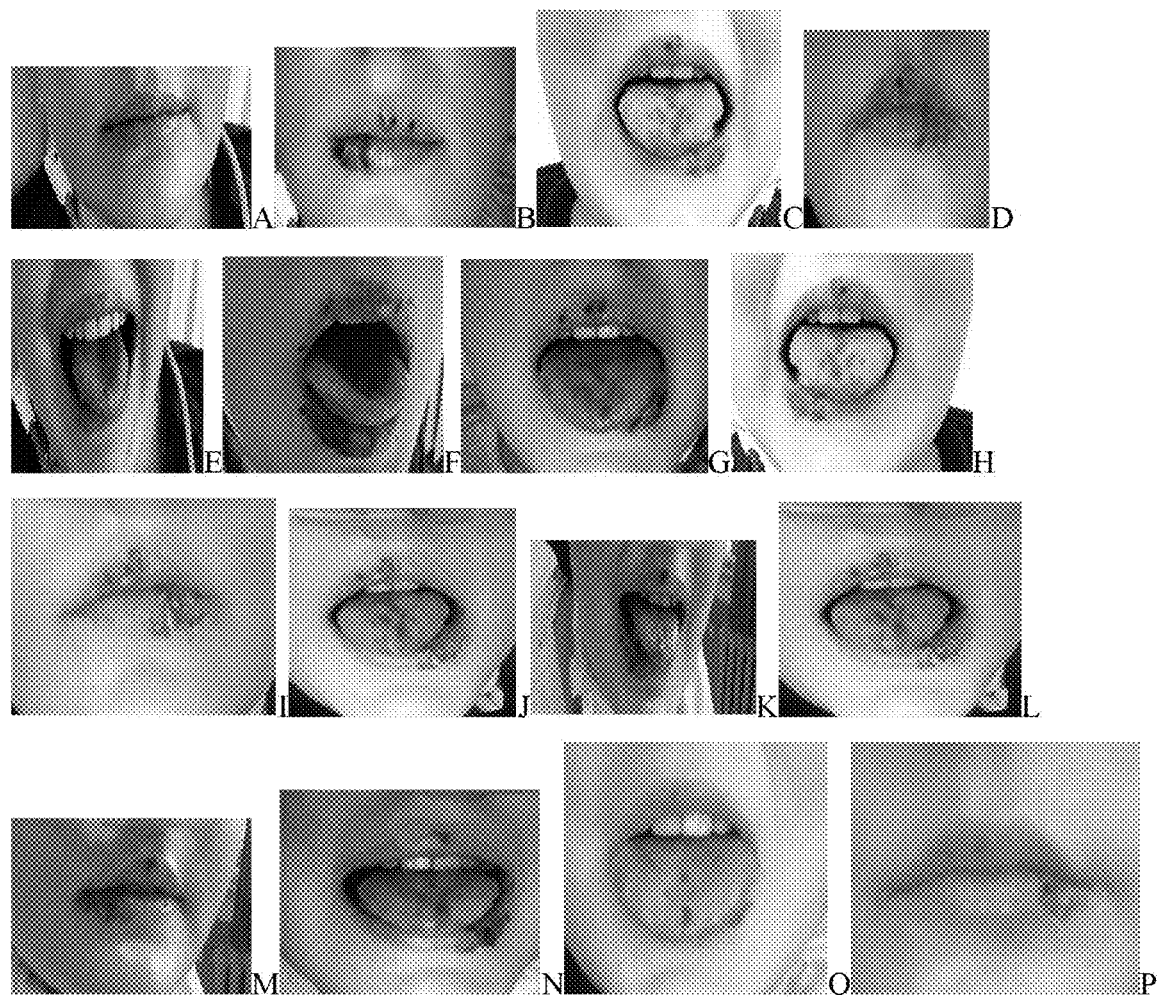
FIG. 3 shows the lesions caused by high dose chemotherapy in a subject diagnosed with Hodgkin's Lymphoma and the healing process once the subject began using the composition comprising the disclosed acidic extract of myrrh resin in the form of gel four times a day. A and B: oral examination of a subject diagnosed with grade IV mucositis performed prior to beginning of treatment revealed multiple bleeding, ulcerated lesions in the upper and lower lip and in palate. C and D: oral examination performed on the first day of treatment. E and F: oral examination performed on the third day of treatment. G and H: oral examination performed on the fourth day of treatment. I and J: oral examination performed on the fifth day of treatment. K and L: oral examination performed on the sixth day of treatment. M and N: oral examination performed on the seventh day of treatment. O and P: oral examination performed after six weeks of treatment showed that mucositis was fully treated.

FIG. 3 shows the lesions caused by high dose chemotherapy in the subject and the healing process once the subject began treatment with the disclosed acidic extract of myrrh resin. A and B: oral examination of a subject diagnosed with grade IV mucositis performed prior to beginning of treatment revealed multiple bleeding, ulcerated lesions in the upper and lower lip and in palate. C and D: oral examination performed on the first day of treatment. E and F: oral examination performed on the third day of treatment. G and H: oral examination performed on the fourth day of treatment. I and J: oral examination performed on the fifth day of treatment. K and L: oral examination performed on the sixth day of treatment. M and N: oral examination performed on the seventh day of treatment. O and P: oral examination performed after six weeks of treatment showed that mucositis was fully treated.

The subject again developed grade IV mucositis after undergoing bone marrow transplant. The subject began using the composition comprising the disclosed acidic extract of myrrh resin in the form of gel four times a day. After a week of applications, the subject showed a strong decrease in mucositis from grade IV to grade II, and began eating solid food. Mucositis was fully treated after two weeks of use.

Example 3: Treatment of Oral Mucositis in Subject with Hodgkin's Lymphoma after Bone Marrow Transplant A subject with Hodgkin's Lymphoma developed grade IV oral mucositis one week after undergoing bone marrow transplant.

Figure 4:
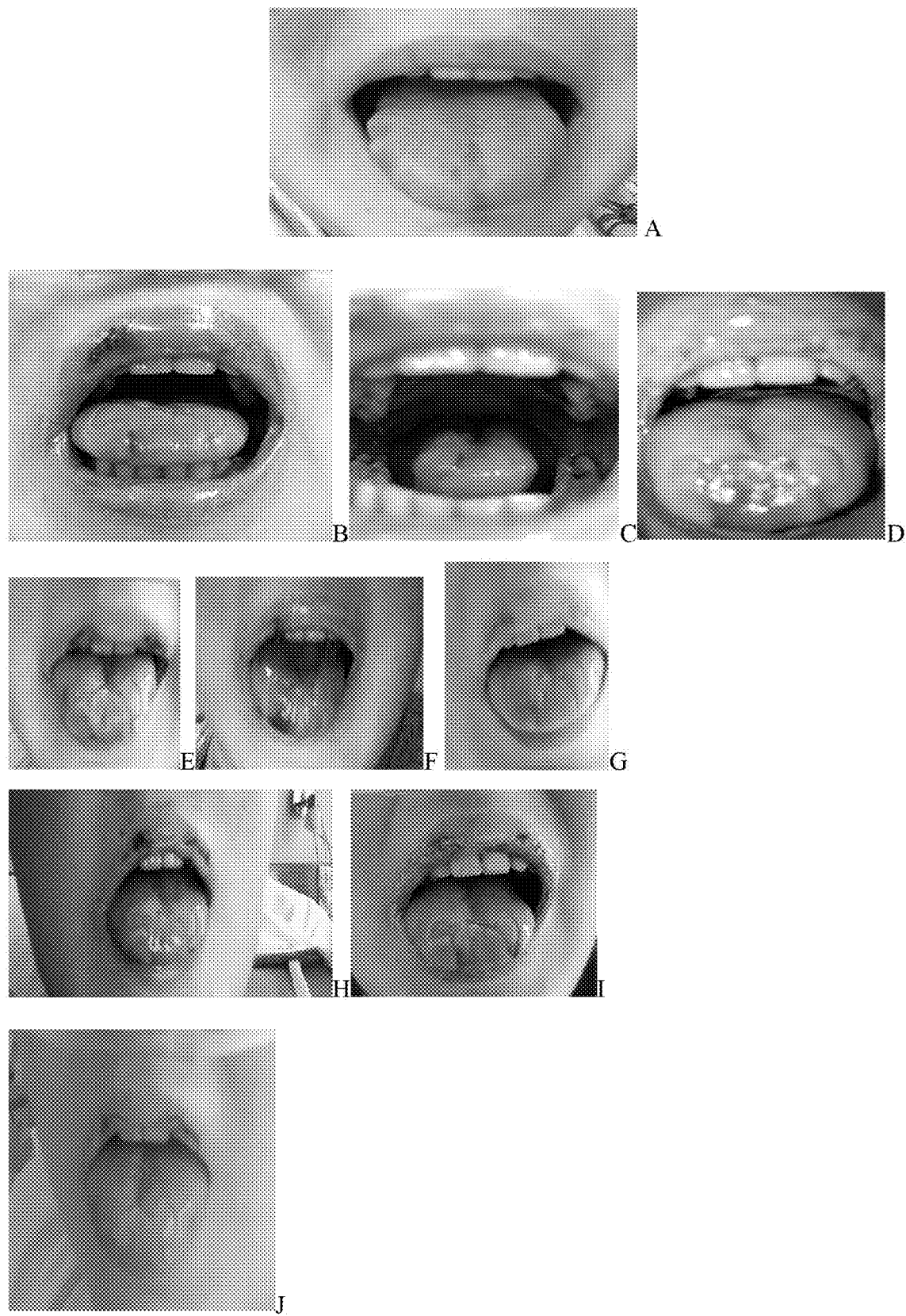
FIG. 4 shows the lesions caused by bone marrow transplant in a subject diagnosed with Hodgkin's Lymphoma and the healing process once the subject began using the composition comprising the disclosed acidic extract of myrrh resin in the form of gel four times a day. A: oral examination performed before transplant showed no signs of mucositis; B, C, D and E: oral examination performed at the end of a two-month period revealed that the subject developed grade IV mucositis after undergoing bone marrow transplant; F: oral examination performed on the first day of treatment with the disclosed acidic extract of myrrh resin. G: oral examination performed on the second day of treatment. H: oral examination performed on the third day of treatment. I: oral examination performed on the fourth day of treatment. J: oral examination performed at the end of the first week of treatment showed a decrease in mucositis from grade IV to grade II. Mucositis was fully treated after two weeks of use (data not shown).

FIG. 4 shows the lesions caused by bone marrow transplant in the subject diagnosed with Hodgkin's Lymphoma and the healing process once the subject began using the composition comprising the disclosed acidic extract of myrrh resin in the form of gel four times a day. A: oral examination performed before transplant showed no signs of mucositis; B, C, D and E: oral examination performed at the end of a two-month period revealed that the subject developed grade IV mucositis after undergoing bone marrow transplant; F: oral examination performed on the first day of treatment with the disclosed acidic extract of myrrh resin. G: oral examination performed on the second day of treatment. H: oral examination performed on the third day of treatment. I: oral examination performed on the fourth day of treatment. J: oral examination performed at the end of the first week of treatment showed a strong decrease in mucositis from grade IV to grade II. Mucositis was fully treated after two weeks of use (data not shown).

Example 4: Treatment of Oral Mucositis in a Subject with Pancreatic Adenocarcinoma and Liver and Pelvis Metastasis Undergoing Chemotherapy Oral examination of a subject diagnosed with pancreatic adenocarcinoma with metastasis in the liver and pelvis, and undergoing chemotherapy revealed multiple bleeding, ulcerated lesions in the upper and lower lip and in palate. The subject was diagnosed with grade IV mucositis and required parenteral or enteral nutritional support. Treatment of the oral lesions with cryotherapy, sodium bicarbonate, Ad-muc, saline solution and chlorhexidine gluconate only caused a mild decrease in mucositis. The subject began using the composition comprising the disclosed acidic extract of myrrh resin in the form of gel four times a day.

Figure 5:
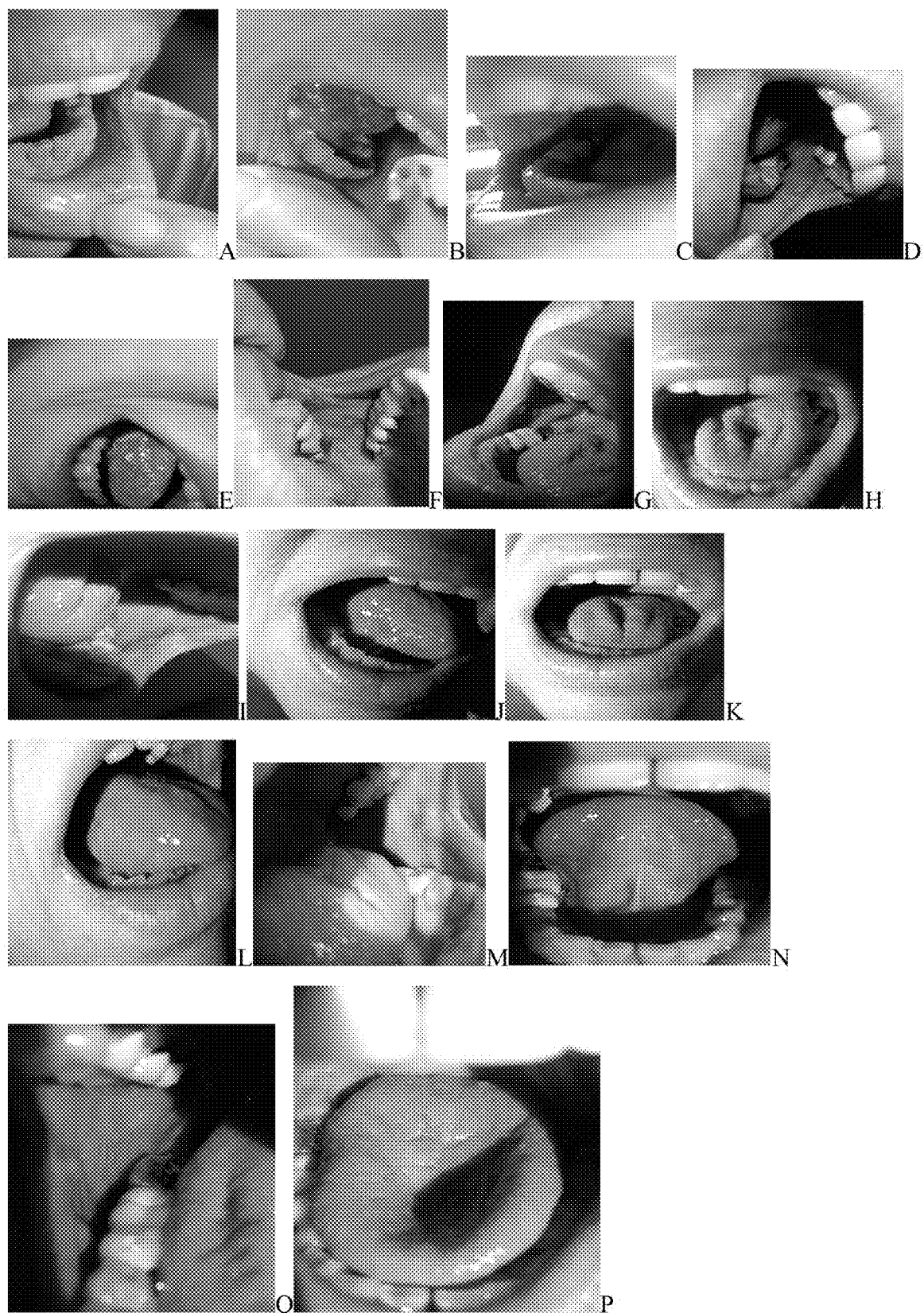
FIG. 5 shows the lesions caused by high dose chemotherapy in a subject diagnosed with pancreatic adenocarcinoma with metastasis in the liver and pelvis, and the healing process once the subject began treatment with the disclosed acidic extract of myrrh resin in the form of gel four times a day. A, B and C: oral examination performed before beginning of treatment revealed multiple bleeding, ulcerated lesions in the upper and lower lip and in palate. The subject was diagnosed with grade IV mucositis. D, E and F: oral examination performed on the first day of treatment. G, H, I and J: oral examination performed on the third day of treatment. K, L and M: oral examination performed on the fifth day of treatment. N, O and P: oral examination performed at the end of the first week of treatment showed a decrease in mucositis from grade IV to grade II. Mucositis was fully treated after two weeks of treatment.

FIG. 5 shows the lesions caused by high dose chemotherapy in the subject diagnosed with pancreatic adenocarcinoma with metastasis in the liver and pelvis, and the healing process once the subject began treatment with the disclosed acidic extract of myrrh resin in the form of gel four times a day. A, B and C: oral examination performed before beginning of treatment revealed multiple bleeding, ulcerated lesions in the upper and lower lip and in palate. The subject was diagnosed with grade IV mucositis. D, E and F: oral examination performed on the first day of treatment. G, H, I and J: oral examination performed on the third day of treatment. K, L and M: oral examination performed on the fifth day of treatment. N, O and P: oral examination performed at the end of the first week of treatment showed a strong decrease in mucositis from grade IV to grade II. After a week of applications, the subject was able to eat solid food. Mucositis was fully treated after two weeks of treatment.

The subject was diagnosed as susceptible to develop oral mucositis and continued to use the composition comprising the disclosed acidic extract of myrrh resin in the form of gel four times a day following three cycles of chemotherapy. The subject underwent the three cycles of chemotherapy without developing mucositis.

Example 5: Treatment of Oral Mucositis in a Subject with Larynx CA Undergoing Chemotherapy Oral examination of a subject diagnosed with Larynx CA and undergoing induction chemotherapy revealed multiple bleeding, and ulcerated lesions in the upper and lower lip and in palate. The subject was diagnosed with grade IV mucositis and required parenteral or enteral nutritional support. Treatment of the oral lesions with cryotherapy, sodium bicarbonate, Ad-muc, saline solution and chlorhexidine gluconate only caused a mild decrease in mucositis. The subject began using the composition comprising the disclosed acidic extract of myrrh resin in the form of gel four times a day.

Figure 8:
FIG. 8 shows the lesions caused by induction chemotherapy in a subject diagnosed with Larinx CA and the healing process once the subject began using the composition comprising the disclosed acidic extract of myrrh resin in the form of gel four times a day. A: oral examination performed prior to beginning of treatment revealed multiple bleeding, ulcerated lesions in the upper and lower lip and in palate. The subject was diagnosed with grade IV mucositis. B: oral examination performed on the first day of treatment. C: oral examination performed on the second day of treatment. D: oral examination performed on the third day of treatment. E: oral examination performed on the fourth day of treatment. F: oral examination performed on the sixth day of treatment showed a decrease in mucositis from grade IV to grade I. Mucositis was fully treated after one week of use and the subject was able to eat solid food.
Figure 8:
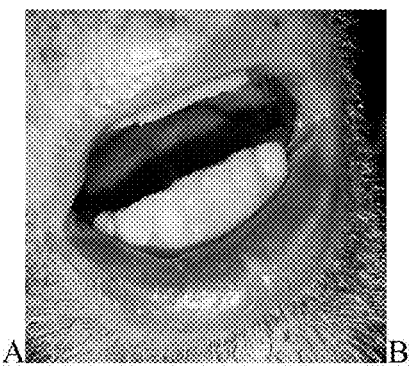
Figure 8:
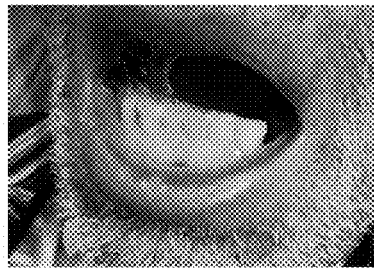
Figure 8:
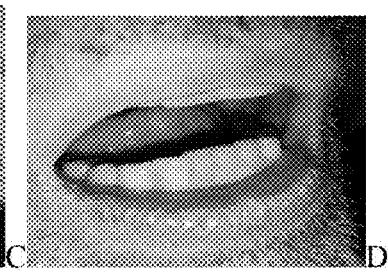
Figure 8:
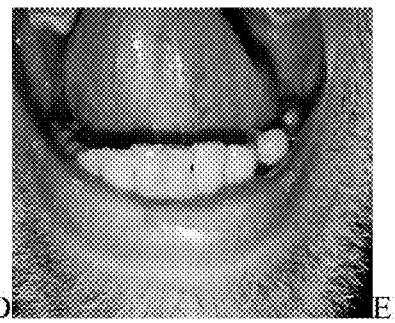
Figure 8:
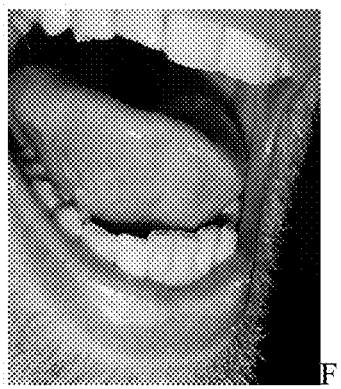

FIG. 8 shows the lesions caused by induction chemotherapy in a subject diagnosed with Larinx CA and the healing process once the subject began using the composition comprising the disclosed acidic extract of myrrh resin in the form of gel four times a day. A: oral examination performed prior to beginning of treatment revealed multiple bleeding, ulcerated lesions in the upper and lower lip and in palate. The subject was diagnosed with grade IV mucositis. B: oral examination performed on the first day of treatment. C: oral examination performed on the second day of treatment. D: oral examination performed on the third day of treatment. E: oral examination performed on the fourth day of treatment. F: oral examination performed on the sixth day of treatment showed a decrease in mucositis from grade IV to grade I. Mucositis was fully treated after one week of use and the subject was able to eat solid food.

Preventive Effects

The following examples show that application of a composition comprising the disclosed acidic extract of myrrh resin in the form of gel is sufficient to prevent the high incidence of oral mucositis brought about by intense radiotherapy.

Figure 6:
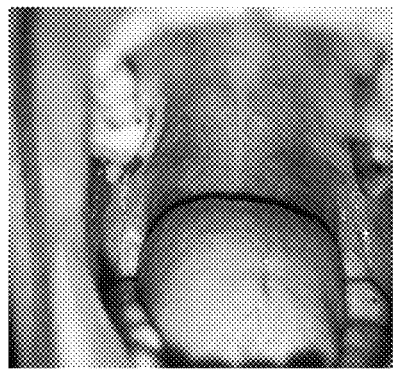
FIG. 6 shows the healing effect of a composition comprising the disclosed acidic extract of myrrh resin in the form of gel four times a day in a subject diagnosed with Larynx Malignant Neoplasma and undergoing radiation therapy. The subject was diagnosed with grade IV mucositis and required parenteral or enteral nutritional support. After a week of applications, the subject showed a decrease in mucositis from grade IV to grade I, and was able to eat solid food.

Example 6: Prevention of Oral Mucositis in a Subject with Larynx Malignant Neoplasma Undergoing Radiation Therapy Oral examination of a subject diagnosed with larynx malignant neoplasma and undergoing radiation therapy revealed multiple bleeding, ulcerated lesions in the upper and lower lip and in palate. The subject was diagnosed with grade IV mucositis. Treatment of the oral lesions with cryotherapy, sodium bicarbonate, Ad-muc, saline solution and chlorhexidine gluconate was not effective. FIG. 6 shows the healing effect of treatment with the disclosed acidic extract of myrrh resin in the form of gel four times a day in the subject diagnosed with Larynx Malignant Neoplasma and undergoing radiation therapy. After a week of applications, the subject presented no signs of mucositis and only symptoms of oral soreness with Grade I erythema.

Figure 7:
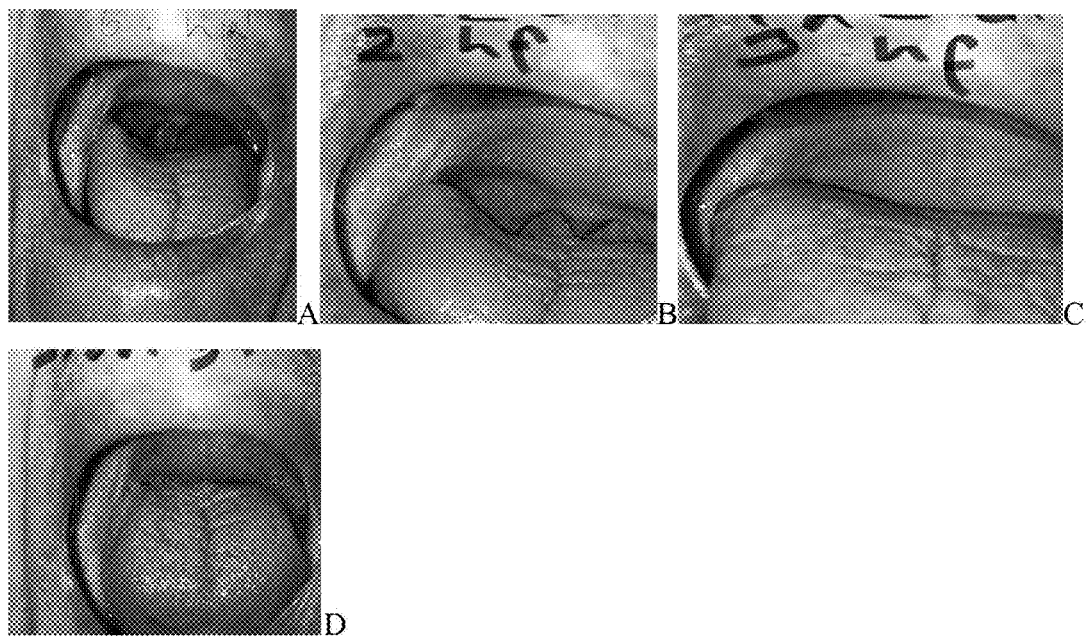
FIG. 7 shows the preventive effect of compositions comprising the disclosed acidic extract of myrrh resin on the development of radiation therapy-induced mucositis in a subject diagnosed with retromolar malignant neoplasma and undergoing radiation therapy. The subject began treatment with a composition comprising the disclosed acidic extract of myrrh resin in the form of gel four times a day at the time the radiation therapy started. A, B, C and D: the subject only developed grade I mucositis, and the symptoms did not prevent the subject from continuing radiation therapy.

Example 7: Prevention of Oral Mucositis in a Subject with Retromolar Malignant Neoplasma Undergoing Radiation Therapy A subject diagnosed with retromolar malignant neoplasma and undergoing radiation therapy began treatment with a composition comprising the disclosed acidic extract of myrrh resin in the form of gel four times a day at the time the radiation therapy started. FIG. 7 shows the preventive effect of treatment with the disclosed acidic extract of myrrh resin on the development of radiation therapy-induced mucositis in the subject A, B, C and D: the subject only developed grade I mucositis, and the symptoms did not prevent the subject from continuing radiation therapy.

Example 8: Prevention of Oral Mucositis in Subject with Breast Cancer Undergoing Mastectomy and Chemotherapy A subject diagnosed with breast cancer undergoing mastectomy and chemotherapy began using the composition comprising the disclosed acidic extract of myrrh resin in the form of gel four times a day at the time she began chemotherapy. The subject completed the full cycle of chemotherapy without developing oral mucositis.

Figure 10:
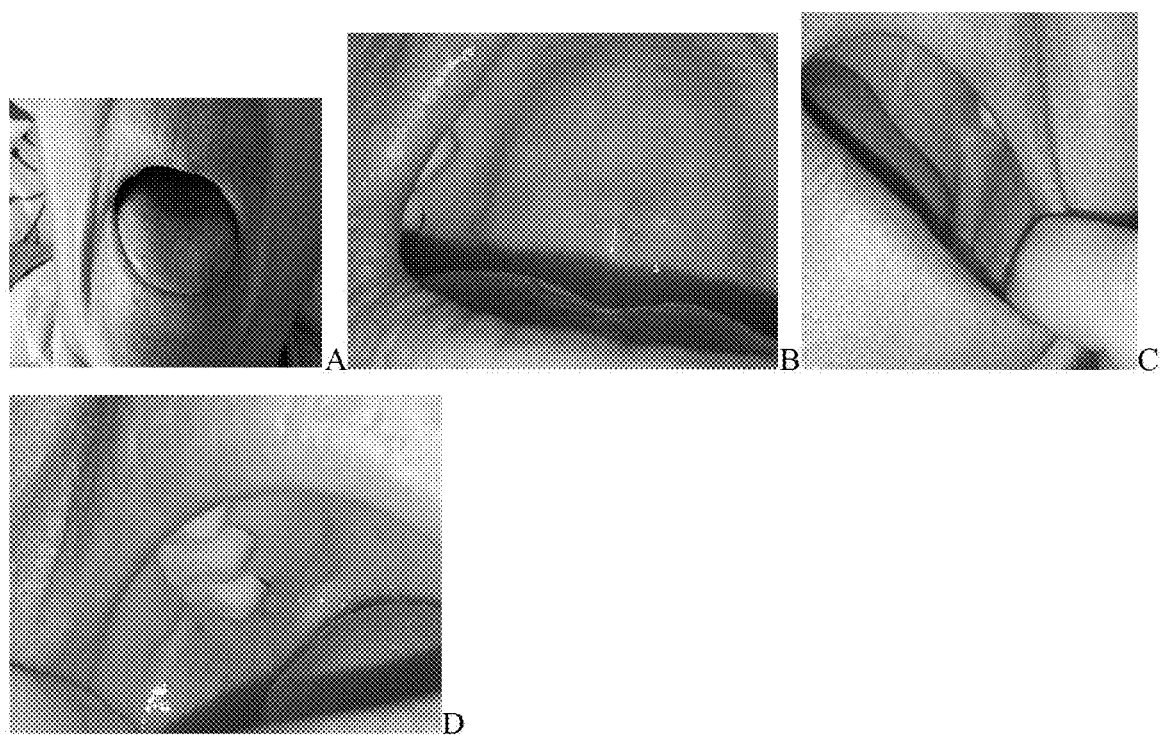
FIG. 10 shows the preventive effect on the development of chemotherapy-induced mucositis in a subject diagnosed with breast cancer undergoing mastectomy and chemotherapy. The subject began using the composition comprising the disclosed acidic extract of myrrh resin in the form of gel four times a day at the time she began chemotherapy. The subject completed the full cycle of chemotherapy without developing oral mucositis. A and B: oral examination performed prior to beginning of treatment; C and D: oral examination performed at the end of the first week of treatment.

FIG. 10 shows the preventive effect on the development of chemotherapy-induced mucositis in a subject diagnosed with breast cancer undergoing mastectomy and chemotherapy. The subject began using the composition comprising the disclosed acidic extract of myrrh resin in the form of gel four times a day at the time she began chemotherapy. The subject completed the full cycle of chemotherapy without developing oral mucositis. A and B: oral examination performed prior to beginning of treatment; C and D: oral examination performed at the end of the first week of treatment.

Example 9: Prevention of Oral Mucositis in a Subject with Buccal Oral Cavity and Pharynx Malignant Neoplasma Undergoing Radiation Therapy A subject diagnosed with buccal oral cavity and pharynx malignant neoplasma and undergoing radiation therapy began treatment with a composition comprising the disclosed acidic extract of myrrh resin in the form of gel four times a day at the time the subject started radiation therapy.

Figure 9:
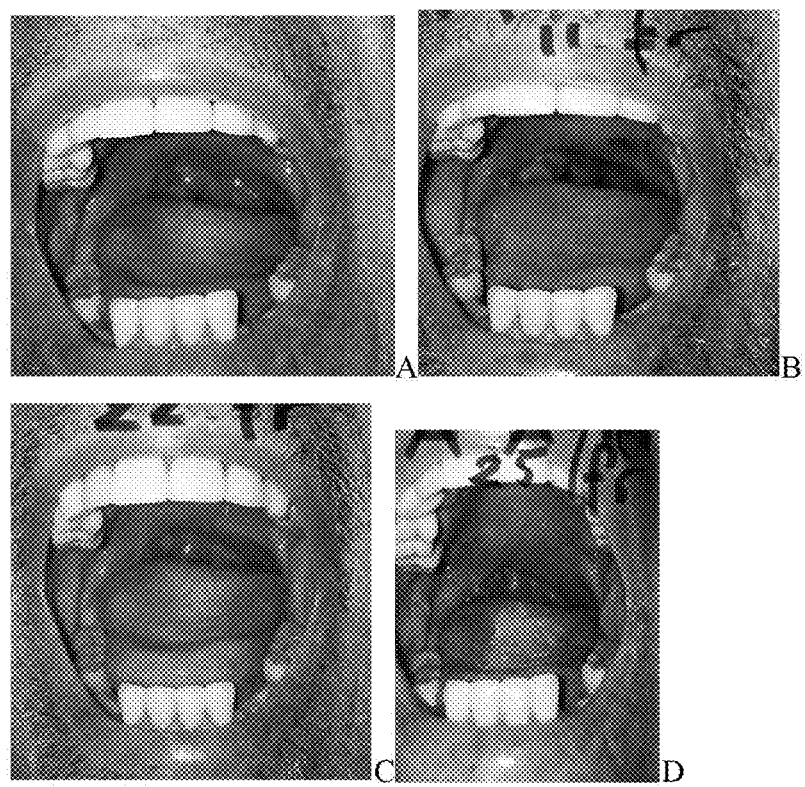
FIG. 9 shows the preventive effect on the development of radiation therapy-induced mucositis in a subject diagnosed with buccal oral cavity and pharynx malignant neoplasma and undergoing radiation therapy. A, B, C and D: the subject began using the composition comprising the disclosed acidic extract of myrrh resin in the form of gel four times a day at the time the radiation therapy started. Oral examination performed on the first day of treatment, two weeks after beginning of treatment, one month after beginning of treatment and two months after beginning of treatment showed that the subject only developed grade I mucositis, and the symptoms did not prevent the subject from continuing radiation therapy.

FIG. 9 shows the preventive effect on the development of radiation therapy-induced mucositis in a subject diagnosed with buccal oral cavity and pharynx malignant neoplasma and undergoing radiation therapy. A, B, C and D: the subject began using the composition comprising the disclosed acidic extract of myrrh resin in the form of gel four times a day at the time the radiation therapy started. Oral examination performed on the first day of treatment, two weeks after beginning of treatment, one month after beginning of treatment and two months after beginning of treatment showed that the subject only developed grade I mucositis, and the symptoms did not prevent the subject from continuing radiation therapy.

Example 10: Effect of the Composition Comprising the Disclosed Acidic Extract of Myrrh Resin on the Incidence and Severity of Oral Mucositis The efficacy and safety of the compositions comprising the disclosed acidic extract of myrrh resin were clinically assessed for prevention, treatment and/or improvement of oral mucositis.

Ten males and six females with confirmed tumors of head and neck who were intended for treatment with radiotherapy (RT) with or without chemotherapy (CT) were included in a single-center, randomized, double-blind, placebo-controlled clinical study. 68.7% of the subjects had oral cavity tumors. Eight subjects were randomized to receive placebo treatment and eight subjects were randomized to receive treatment with the disclosed myrrh resin composition. The subjects ranged in age between 36 and 85 years old, with a mean age of 65.3 years. Pathological types were mostly squamous cell (81%). Eleven subjects (68.5%) had locally advanced cancer. The mean delivered radiation dose was 64.8 Gray (Gy) in a 33 fraction (fr) (range, 50-70 Gy/25-38 fr). Three subjects were concurrently treated with chemotherapy. The myrrh resin composition was applied four times a day in form of gel on the oral mucosa. The composition was administered by swirling in the mouth of each subject for 15 minutes before the subject was allowed to swallow it. Subjects were evaluated on a weekly basis and follow-up forms were completed and assessed during and at the end of treatment. WHO and EORTC/RTOG scales were used to determine the severity of mucositis and confirmed with pictures of the affected areas.

Upon evaluation, subjects treated with the myrrh resin gel completed radiotherapy with no symptoms of oral mucositis. All subjects treated with placebo developed grade 3 mucositis within the third week of treatment. Once switched to treatment with the myrrh resin gel, these subjects showed a decrease from grade 3 to grade 2 in oral mucositis ulcerations. None of the subjects treated with the myrrh resin gel showed signs of grade 3 mucositis. All subjects treated with placebo required additional opioid treatment and enteral food solution feeding.

These results indicate that treatment with compositions comprising the disclosed acidic extract of myrrh resin effectively decreases the incidence and severity of oral mucositis in subjects undergoing radiation therapy.

Example 11: Antioxidant Activity of the Disclosed Acidic Extract of Myrrh Resin

The antioxidant activity of the acidic myrrh extract was evaluated using 2.2-diphenyl-1-hydrazyl (DPPH) as a free radical substrate. In its radical form, DPPH has an absorption band at 515 nm, which disappears upon reduction by an antiradical compound. Solutions of different concentrations of the myrrh extract in methanol (0.1 ml) were added to 3.9 ml of a $6\times10^{-5}$ methanol DPPH solution. The exact initial DPPH concentration (CDPPH) in the reaction medium was calculated from a calibration curve with the equation $Abs_{515nm}=12,509\times(CDPPH)-2.58\times10^{-3}$ as determined by linear regression. The decrease in absorbance was determined at 515 nm after 1 hour incubation. Absorbance was measured twice for each extract concentration tested. Then, for each extract concentration tested, percentage oxidation inhibition was calculated according to the formula: % scavenged radical=[1−absorbance of sample/absorbance of control]×100.

Figure 11:
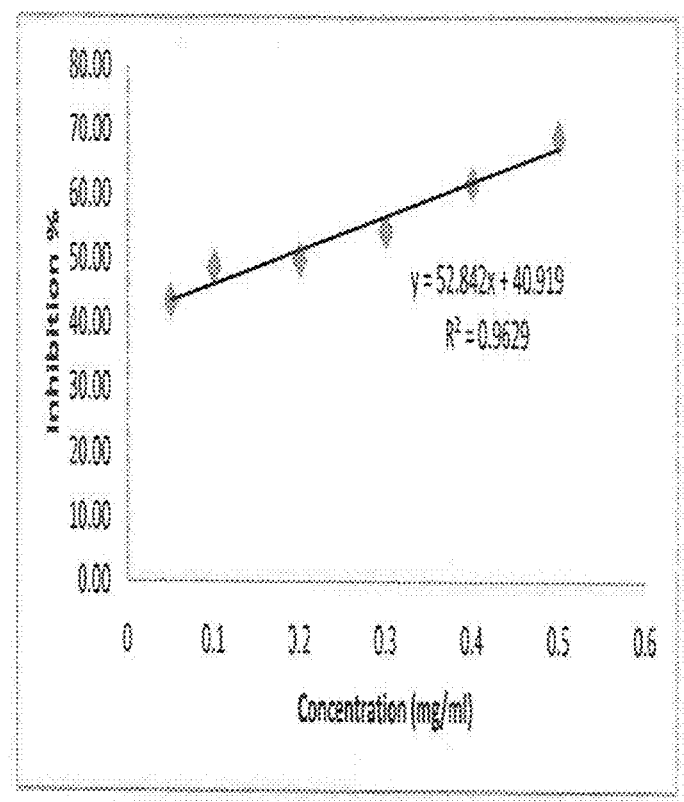
FIG. 11 is a plot showing the antioxidant activity of the disclosed myrrh extract expressed as percentage of oxidation inhibition in relation to extract concentration.

The results are shown in Table 2 below and FIG. 11. 50% Inhibitory Concentration ($IC_{50}$) was 0.17.

These results indicate that the higher the concentration of the myrrh extract, the more absorbance decreases and percentage oxidation inhibition increases. These data indicate that the disclosed acetic myrrh extract has high antioxidant activity.

TABLE 2

| Concentration | Absorbance | Absorbance | Average Absorbance | % Inhibition |
| --- | --- | --- | --- | --- |
| Blank | 1.6339 | 1.5973 | 1.6156 | 0.00 |
| 0.05 | 0.9108 | 0.9192 | 0.9150 | 43.36 |
| 0.1 | 0.8095 | 0.8471 | 0.8283 | 48.73 |
| 0.2 | 0.8178 | 0.7991 | 0.8085 | 49.96 |
| 0.3 | 0.7323 | 0.7369 | 0.7346 | 54.53 |
| 0.4 | 0.6301 | 0.6014 | 0.6158 | 61.89 |
| 0.5 | 0.4976 | 0.5059 | 0.5018 | 68.94 |

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

The invention claimed is:
1. A composition comprising:
an acetic acid extract of myrrh resin of about 5% to 50% (w/w) of the composition, wherein the acetic acid extract comprises polysaccharides and sesquiterpenes, wherein the polysaccharides comprise one or more of ribofuranose, arabinopyranose, ribopyranose, uronic acid, mannopyranose, allofuronase, galacturonic acid, galactopyranose and allopyranose in a concentration of about 20% to about 40% (w/w) of the acetic acid extract, wherein the sesquiterpenes are in a concentration of about 40% to about 80% (w/w) of the acetic acid extract;
a hydrocolloid of about 1% to 5% (w/w) of the composition, wherein the hydrocolloid is one or more of starch, xanthan gum, guar gum, locust bean gum, gum karaya, gum tragacanth, gum Arabic, cellulose, alginate, pectin, carrageenan, gelatin, gellan and agar; and
a pH adjuster of about 0.1 to 1.0% (w/w) of the composition, wherein the composition has a pH in the range of about 3.0 and 5.0.
2. The composition of claim 1, wherein the pH adjuster is one more of ammonium bicarbonate, ammonium carbonate, ammonium citrate, ammonium hydroxide, ammonium phosphate, calcium carbonate, calcium chloride, calcium citrate, calcium fumarate, calcium hydroxide; calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

3. The composition of claim 2, the acetic acid extract of myrrh resin comprises 40-50% (w/w) furanoeudesma-1,3-dien, 10-15% (w/w) lindestrene and 5-10% (w/w) curzerene.

4. The composition of claim 3, wherein the acetic acid is in form of vinegar, and wherein the vinegar is unpasteurized and unfiltered apple cider vinegar.

5. The composition of claim 4, wherein the acetic acid extract of myrrh resin comprises myrrh resin and apple cider vinegar in a ratio of 1:4.

6. The composition of claim 1, wherein the composition comprises about 30% (w/w) of myrrh resin extract; about 3% (w/w) of xanthan gum; and about 0.5% of calcium carbonate, and wherein the composition further comprises a preservative selected from one or more of a benzoate, a nitrite, a sulphite and a sorbate.

7. The composition of claim 6, wherein the preservative is sodium benzoate.

8. The composition of claim 1, wherein the composition is a Newtonian fluid in form of a mouthwash, a cream, a gel, or a wound healing composition.

9. The composition of claim 8, wherein the mouthwash further comprises an excipient, and wherein the excipient is one or more of betaine anhydrous, glycerin, a thymol extract, a clove extract, a mint extract, a fruit flavor, and a *Stevia* powder.

10. The composition of claim 9, wherein the mouthwash comprises 2-6% (w/w) betaine anhydrous; 1-10% (w/w) glycerin; 0.01-0.1% (w/w) thymol extract; 0.5-1% (w/w) clove extract; 0.5-1% (w/w) mint extract; 0.5-1% (w/w) fruit flavor; and 0.1-0.5% (w/w) *Stevia* powder.

11. The composition of claim 8, wherein the composition is a cream having a density between about 1.059 and about 1.015 g/cm$^3$ and a viscosity between about 130,200 and about 166,700 centipoise at room temperature, wherein the composition further comprises an excipient in a concentration between about 10% and about 18%, and wherein the excipient is one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

12. The composition of claim 11, wherein the cream comprises 5-10% (w/w) zinc oxide; 4-8% (w/w) *Hypericum perforatum* oil; 3-8% (w/w) Cera alba; 2-5% (w/w) *Prunus amygdalus sativa* kernel oil; 2-5% (w/w) *Theobroma cacao* seed butter; and 0.5-1.5% (w/w) allantoin.

13. The composition of claim 8, wherein the composition is a gel having a density between about 0.9185 and about 1.0521 g/cm$^3$ and a viscosity between about 30,900 and about 33,900 centipoise at room temperature.

14. A process of preparing an acidic myrrh resin extract enriched in sesquiterpenes and polysaccharides, wherein the process comprises: (1) collecting myrrh resin from *Commiphora molmol*; (2) drying the myrrh resin at a temperature between −10° C. to about −4° C. for a period of time between 24 and 72 hours; (3) dissolving the dried myrrh resin in acidic solvent to obtain a solution; (4) filtering the solution to collect an extract; (5) filtering and cooling the extract; and (6) adjusting the extract's pH to a pH range between about 3.0 and about 5.0 with a pH adjuster to obtain an acidic extract of myrrh resin enriched in sesquiterpenes and polysaccharides.

15. The process of claim 14, wherein the process further comprises (8) adding a hydrocolloid to the extract; and (9) adjusting the extract's pH to a pH range between about 3.0 and about 5.0 with a pH adjuster to obtain a composition comprising an acidic extract of myrrh resin enriched in sesquiterpenes and polysaccharides.

16. The process of claim 15, wherein the acidic solvent is vinegar, and wherein the vinegar is unpasteurized and unfiltered apple cider vinegar.

17. The process of claim 16, wherein the myrrh resin and the apple cider vinegar are in a ratio of 1:4.

18. The process of claim 17, wherein the hydrocolloid is one or more of starch, xanthan gum, guar gum, locust bean gum, gum karaya, gum tragacanth, gum Arabic, cellulose, alginate, pectin, carrageenan, gelatin, gellan and agar.

19. The process of claim 18, wherein the pH adjuster is one or more of ammonium bicarbonate, ammonium carbonate, ammonium citrate, ammonium hydroxide, ammonium phosphate, calcium carbonate, calcium chloride, calcium citrate, calcium fumarate, calcium hydroxide, calcium phosphate, magnesium carbonate, magnesium citrate, magnesium hydroxide, magnesium phosphate, magnesium sulfate, potassium bicarbonate, potassium carbonate, potassium citrate, potassium fumarate, potassium hydroxide, potassium sulfate, sodium bicarbonate, sodium carbonate, sodium citrate, sodium fumarate, sodium hydroxide, and sodium phosphate.

20. The process of claim 19, wherein the hydrocolloid is xanthan gum and the pH adjuster is calcium carbonate, and wherein the composition has a pH between about 3.5 and 4.5.

21. The process of claim 20, wherein the composition comprises about 5 to 50% (w/w) of myrrh resin extract; about 1 to about 5% (w/w) of xanthan gum; and about 0.1 to about 1.0% of calcium carbonate.

22. The process of claim 21, wherein the composition comprises about 30% (w/w) of myrrh resin extract; about 3% (w/w) of xanthan gum; and about 0.5% of calcium carbonate.

23. The process of claim 22, wherein the composition is in form of a Newtonian fluid, and wherein the process further comprises adding one or more of a preservative, an excipient or gelling agent to produce a mouthwash, a cream, a gel, a food product or a wound healing composition.

24. The process of claim 23, wherein the preservative is one or more of a benzoate, a nitrite, a sulphite and a sorbate, and wherein the excipient is one or more of betaine anhydrous, glycerin, a thymol extract, a clove extract, a mint extract, a fruit flavor, a *Stevia* powder, water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

25. The process of claim 24, wherein the mouthwash comprises 2-6% (w/w) betaine anhydrous; 1-10% (w/w)

glycerin; 0.01-0.1% (w/w) thymol extract; 0.5-1% (w/w) clove extract; 0.5-1% (w/w) mint extract; 0.5-1% (w/w) fruit flavor; and 0.1-0.5% (w/w) *Stevia* powder.

26. The process of claim 24, wherein the cream has a density between about 1.059 and about 1.015 g/cm$^3$, and a viscosity between about 130,200 and about 166,700 centipoise at room temperature, and wherein the cream comprises 5-10% (w/w) zinc oxide; 4-8% (w/w) *Hypericum perforatum* oil; 3-8% (w/w) Cera alba; 2-5% (w/w) *Prunus amygdalus sativa* kernel oil; 2-5% (w/w) *Theobroma cacao* seed butter; and 0.5-1.5% (w/w) allantoin.

27. The process of claim 24, wherein the gel has a density between about 0.9185 and about 1.0521 g/cm$^3$, and a viscosity between about 30,900 and about 33,900 centipoise at room temperature.

28. The process of claim 24, wherein the food product is a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

29. A method for treating, managing or preventing oral mucositis in a subject in need thereof, wherein the method comprises topically administering to the subject's oral mucosa the composition of claim 8.

30. The method of claim 29, wherein the composition is in form of a mouthwash comprising 2-6% (w/w) betaine anhydrous; 1-10% (w/w) glycerin; 0.01-0.1% (w/w) thymol extract; 0.5-1% (w/w) clove extract; 0.5-1% (w/w) mint extract; 0.5-1% (w/w) fruit flavor; and 0.1-0.5% (w/w) *Stevia* powder.

31. The method of claim 29, wherein the composition is in form of a gel having a density between about 0.9185 and about 1.0521 g/cm$^3$, and a viscosity between about 30,900 and about 33,900 centipoise at room temperature.

32. The method of claim 29, wherein the composition is in form of a food product, and wherein the food product is a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

33. A method of treating, managing or preventing an inflammation, an ulcer or a wound in a subject in need thereof, wherein the method comprises administering to the subject the composition of claim 1.

34. The method of claim 33, wherein the ulcer is a mucosal ulcer, an oral mucosal ulcer, or a gastrointestinal ulcer.

35. The method of claim 33, wherein the inflammation is gastrointestinal mucositis, a canker sore, or Behcet disease.

36. The method of claim 33, wherein the wound is a chronic wound, an abrasion, a furuncle or a skin inflammation.

37. The method of claim 33, wherein the composition is in form of a mouthwash, and wherein the mouthwash further comprises an excipient selected from one or more of betaine anhydrous, glycerin, a thymol extract, a clove extract, a mint extract, a fruit flavor, and a *Stevia* powder.

38. The method of claim 37, wherein the mouthwash comprises 2-6% (w/w) betaine anhydrous; 1-10% (w/w) glycerin; 0.01-0.1% (w/w) thymol extract; 0.5-1% (w/w) clove extract; 0.5-1% (w/w) mint extract; 0.5-1% (w/w) fruit flavor; and 0.1-0.5% (w/w) *Stevia* powder.

39. The method of claim 33, wherein the composition is in form of a cream which further comprises an excipient in a concentration between about 10% and about 18%, and wherein the excipient is one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

40. The method of claim 39, wherein the cream has a density between about 1.059 and about 1.015 g/cm$^3$, and a viscosity between about 130,200 and about 166,700 centipoise at room temperature, and wherein the cream comprises 5-10% (w/w) zinc oxide; 4-8% (w/w) *Hypericum perforatum* oil; 3-8% (w/w) Cera alba; 2-5% (w/w) *Prunus amygdalus sativa* kernel oil; 2-5% (w/w) *Theobroma cacao* seed butter; and 0.5-1.5% (w/w) allantoin.

41. The method of claim 33, wherein the composition is in form of a gel having a density between about 0.9185 and about 1.0521 g/cm$^3$, and a viscosity between about 30,900 and about 33,900 centipoise at room temperature.

42. The method of claim 33, wherein the food product is a dairy product, a yoghurt, an ice cream, a milk-based drink, a milk-based garnish, a pudding, a milkshake, an ice tea, a fruit juice, a diet drink, a soda, a sports drink, a powdered drink mixture for dietary supplementation, an infant and baby food, a calcium-supplemented orange juice, a sauce or a soup.

43. The method of claim 33, wherein the composition is administered to the subject once a day, twice a day, three times a day, or four times a day, in a therapeutically effective amount from about 350 mg to about 600 mg/day.

44. The method of claim 43, wherein the subject is a mammal.

45. The method of claim 44, wherein the subject is a human subject.

46. The method of claim 45, wherein the composition is administered to the subject prior to, during or after exposure to radiation or chemotherapy.

47. A method of treating, managing or preventing a topical inflammation in a subject in need thereof, wherein the method comprises administering to the subject the composition of claim 8.

48. The method of claim 47, wherein the topical inflammation is a bed sore, decubitis or an acute or chronic wound inflammation.

49. The method of claim 48, wherein the composition is in form of a cream which further comprises an excipient in a concentration between about 10% and about 18%, and wherein the excipient is one or more of water, zinc oxide, *Hypericum perforatum* oil, cera alba, PEG-7, glyceryl cocoate, glycerin, *Prunus amygdalus sativa* kernel oil, ethylhexyl stearate, cetyl alcohol, coco-caprylate, *Theobroma cacao* seed butter, glyceryl stearate, allantoin, aloe barbadensis leaf juice, tocopheryl acetate, panthenol, cetearyl alcohol, hydrogenated palm kernel glycerides, hydrogenated palm glyceride, stearic acid, dicaprylyl ether, sodium lauroyl glutamate, cetearyl olivate, phenoxyethanol, ethylhexyl glycerine, and sorbitan olivate.

50. The method of claim 49, wherein the cream has a density between about 1.059 and about 1.015 g/cm$^3$, and a viscosity between about 130,200 and about 166,700 centipoise at room temperature, and wherein the cream comprises 5-10% (w/w) zinc oxide; 4-8% (w/w) *Hypericum perforatum* oil; 3-8% (w/w) Cera alba; 2-5% (w/w) *Prunus amygdalus sativa* kernel oil; 2-5% (w/w) *Theobroma cacao* seed butter; and 0.5-1.5% (w/w) allantoin.

51. The method of claim 48, wherein the composition is in form of a gel having a density between about 0.9185 and about 1.0521 g/cm$^3$, and a viscosity between about 30,900 and about 33,900 centipoise at room temperature.

52. The method of claim 48, wherein the composition is administered to the subject once a day, twice a day, three times a day, or four times a day, in a therapeutically effective amount.

53. The method of claim 52, wherein the subject is a mammal.

54. The method of claim 53, wherein the subject is a human subject.

55. The method of claim 54, wherein the composition is administered to the subject prior to, during or after exposure to radiation or chemotherapy.

\* \* \* \* \*